IIIIII

US009220502B2

(12) United States Patent
Zemlok et al.

(10) Patent No.: US 9,220,502 B2
(45) Date of Patent: Dec. 29, 2015

(54) STAPLE FORMATION RECOGNITION FOR A SURGICAL DEVICE

(71) Applicant: Covidien LP, Mansfield, MA (US)

(72) Inventors: Michael A. Zemlok, Prospect, CT (US); Russell Pribanic, Roxbury, CT (US); Adam J. Ross, Prospect, CT (US)

(73) Assignee: Covidien LP, Mansfield, MA (US)

( * ) Notice: Subject to any disclaimer, the term of this patent is extended or adjusted under 35 U.S.C. 154(b) by 509 days.

(21) Appl. No.: 13/685,734

(22) Filed: Nov. 27, 2012

(65) Prior Publication Data

US 2013/0168431 A1 Jul. 4, 2013

Related U.S. Application Data

(60) Provisional application No. 61/580,753, filed on Dec. 28, 2011.

(51) Int. Cl.
| | |
|---|---|
| *A61B 17/04* | (2006.01) |
| *A61B 17/10* | (2006.01) |
| *A61B 17/068* | (2006.01) |
| *A61B 17/072* | (2006.01) |
| A61B 17/064 | (2006.01) |
| A61B 17/00 | (2006.01) |
| A61B 19/00 | (2006.01) |

(52) U.S. Cl.
CPC ......... *A61B 17/068* (2013.01); *A61B 17/07207* (2013.01); *A61B 17/0644* (2013.01); *A61B 2017/0003* (2013.01); *A61B 2017/00929* (2013.01); *A61B 2017/07257* (2013.01); *A61B 2017/07264* (2013.01); *A61B 2019/4836* (2013.01)

(58) Field of Classification Search
CPC ........... A61B 2017/07278; A61B 2017/07264; A61B 2017/07257; A61B 2019/465; A61B 2019/4857; A61B 2019/4836; A61B 2017/00022; A61B 2019/448; A61B 19/5244; A61B 2017/00212; A61B 17/068
USPC .................... 227/175.1–182.1; 606/142–143, 606/219–221
See application file for complete search history.

(56) References Cited

U.S. PATENT DOCUMENTS

| | | | | |
|---|---|---|---|---|
| 4,467,805 A | * | 8/1984 | Fukuda | A61B 17/0644 606/217 |
| 4,485,816 A | * | 12/1984 | Krumme | A61B 17/0644 219/201 |
| 4,531,522 A | * | 7/1985 | Bedi | A61B 17/0644 606/220 |
| 4,550,870 A | * | 11/1985 | Krumme et al. | 227/19 |
| 4,887,601 A | * | 12/1989 | Richards | A61B 17/0644 411/457 |

(Continued)

OTHER PUBLICATIONS

European Search Report dated Mar. 14, 2013, 6 pages.

*Primary Examiner* — Robert Long

(57) ABSTRACT

There is provided a surgical stapler having a staple formation recognition system incorporated into an anvil member of the surgical stapler. In one series of embodiments, a trace system and controller form an open electrical circuit and a surgical staple acts as an electrical connector to complete an electrical circuit and confirm the proper formation of the surgical staple. In another series of embodiments, a trace system and a controller form a complete electrical circuit which is broken by engagement of a surgical staple with a trace pad of the trace system to signal proper formation of the surgical staple. There is also provided a knife blade position indication system for tracking the progress of a knife blade through the anvil member and relative to staple crimping pockets formed in the anvil member.

20 Claims, 14 Drawing Sheets

(56) References Cited

U.S. PATENT DOCUMENTS

| | | | |
|---|---|---|---|
| 5,026,390 A * | 6/1991 | Brown | A61B 17/083 411/457 |
| 5,106,066 A * | 4/1992 | Shea | B27F 7/28 227/131 |
| 5,209,756 A * | 5/1993 | Seedhom | A61B 17/0642 606/151 |
| 5,242,457 A * | 9/1993 | Akopov | A61B 17/064 227/175.1 |
| 5,383,880 A | 1/1995 | Hooven | |
| 5,389,098 A * | 2/1995 | Tsuruta et al. | 606/41 |
| 5,395,033 A | 3/1995 | Byrne et al. | |
| 5,464,144 A * | 11/1995 | Guy | A61B 17/072 128/104.1 |
| 5,486,187 A * | 1/1996 | Schenck | A61B 17/11 606/151 |
| 5,489,058 A * | 2/1996 | Plyley | A61B 17/064 227/176.1 |
| 5,503,320 A | 4/1996 | Webster et al. | |
| 5,518,163 A | 5/1996 | Hooven | |
| 5,518,164 A * | 5/1996 | Hooven | 227/5 |
| 5,535,934 A | 7/1996 | Boiarski et al. | |
| 5,535,937 A | 7/1996 | Boiarski et al. | |
| 5,562,239 A | 10/1996 | Boiarski et al. | |
| 5,738,474 A * | 4/1998 | Blewett | A61B 17/07207 411/473 |
| 5,785,713 A * | 7/1998 | Jobe | A61B 17/0401 606/101 |
| 5,893,506 A | 4/1999 | Powell | |
| 5,947,999 A * | 9/1999 | Groiso | A61B 17/0642 606/216 |
| 5,992,724 A * | 11/1999 | Snyder | 227/120 |
| 6,315,184 B1 * | 11/2001 | Whitman | A61B 17/07207 227/176.1 |
| 6,671,185 B2 | 12/2003 | Duval | |
| 7,077,856 B2 | 7/2006 | Whitman | |
| 7,438,209 B1 | 10/2008 | Hess et al. | |
| 7,464,847 B2 | 12/2008 | Viola et al. | |
| 7,559,453 B2 * | 7/2009 | Heinrich et al. | 227/180.1 |
| 7,959,053 B2 * | 6/2011 | Yasuda | A61B 17/0644 227/175.1 |
| 8,308,041 B2 * | 11/2012 | Kostrzewski | A61B 17/07207 227/175.1 |
| 8,348,972 B2 * | 1/2013 | Soltz | A61B 17/0644 227/175.1 |
| 8,453,908 B2 * | 6/2013 | Bedi | A61B 17/0644 227/176.1 |
| 8,596,515 B2 * | 12/2013 | Okoniewski | 227/176.1 |
| 8,636,191 B2 * | 1/2014 | Meagher | A61B 17/0644 227/179.1 |
| 8,657,174 B2 * | 2/2014 | Yates | 227/175.1 |
| 8,720,766 B2 * | 5/2014 | Hess | A61B 17/0644 227/175.1 |
| 8,721,646 B2 * | 5/2014 | Fox | A61B 17/0642 606/75 |
| 8,727,197 B2 * | 5/2014 | Hess | 227/176.1 |
| 2002/0029044 A1 * | 3/2002 | Monassevitch | A61B 17/0642 606/75 |
| 2004/0245307 A1 | 12/2004 | Haramiishi | |
| 2005/0070958 A1 | 3/2005 | Swayze et al. | |
| 2005/0184121 A1 * | 8/2005 | Heinrich | 227/175.1 |
| 2006/0097025 A1 | 5/2006 | Milliman et al. | |
| 2006/0231583 A1 * | 10/2006 | Kumayama | 227/134 |
| 2007/0102472 A1 * | 5/2007 | Shelton, IV | 227/175.1 |
| 2008/0078808 A1 * | 4/2008 | Hess | A61B 17/0644 227/181.1 |
| 2008/0312687 A1 * | 12/2008 | Blier | 606/219 |
| 2009/0054908 A1 | 2/2009 | Zand et al. | 606/130 |
| 2009/0134199 A1 | 5/2009 | Heinrich et al. | |
| 2009/0234248 A1 | 9/2009 | Zand et al. | |
| 2010/0096435 A1 * | 4/2010 | Fuchs et al. | 227/179.1 |
| 2011/0036887 A1 * | 2/2011 | Zemlok | A61B 17/07207 227/175.1 |
| 2011/0309128 A1 * | 12/2011 | Okoniewski | 227/176.1 |
| 2012/0228358 A1 | 9/2012 | Zemlok et al. | 227/176.1 |
| 2013/0008935 A1 * | 1/2013 | Brusaw et al. | 227/4 |
| 2014/0054355 A1 * | 2/2014 | Okoniewski | 227/176.1 |

\* cited by examiner

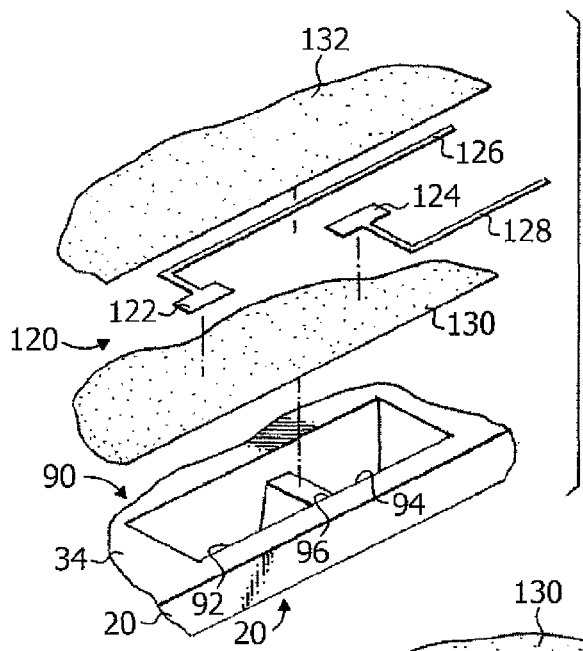
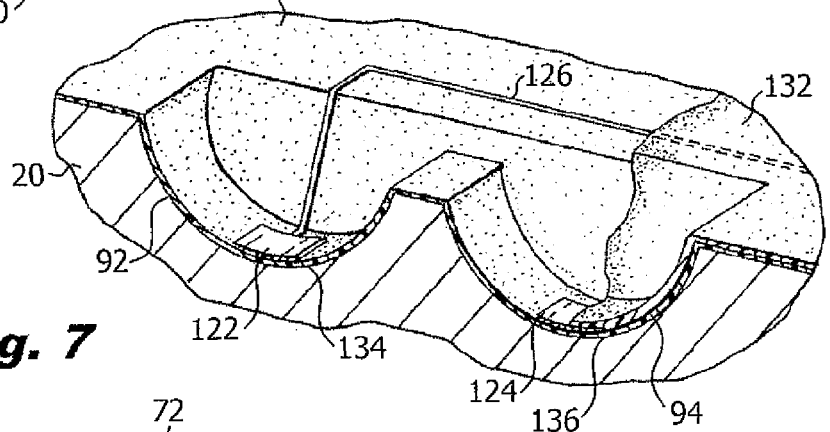
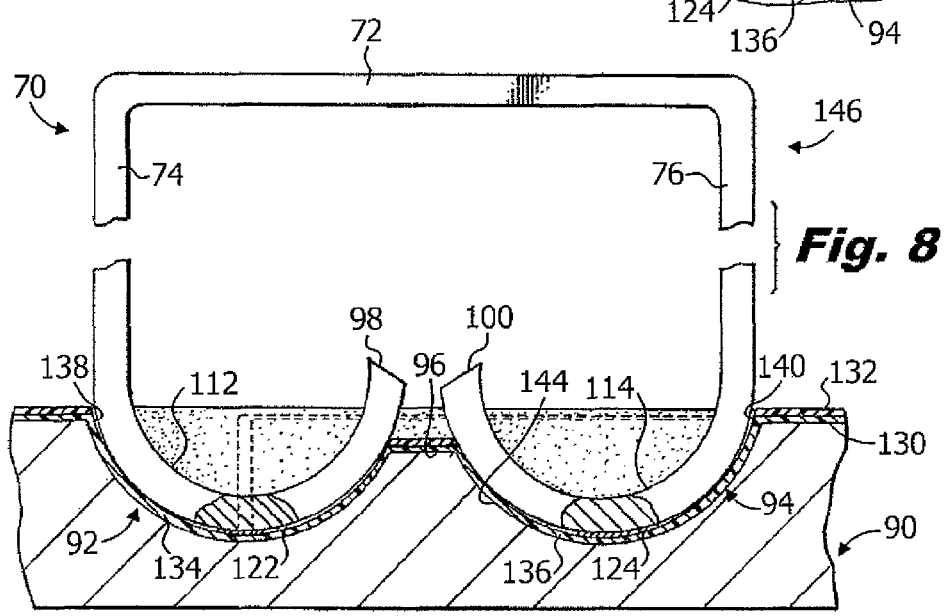

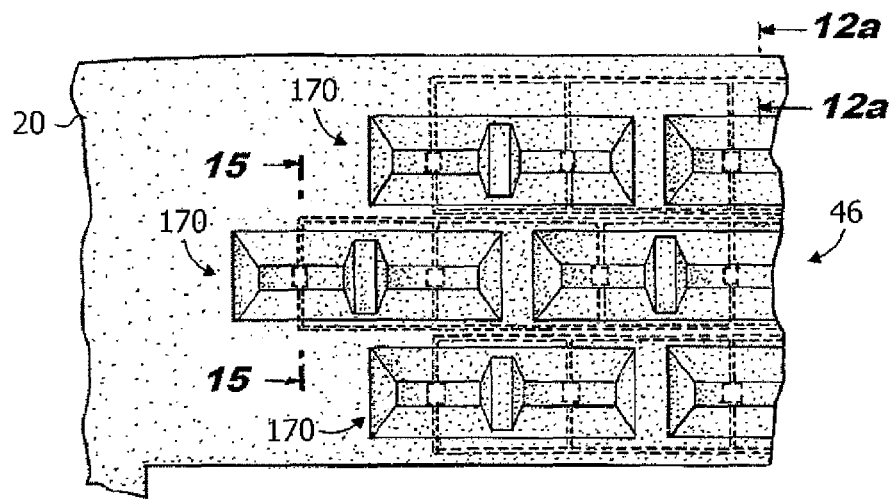
Fig. 12
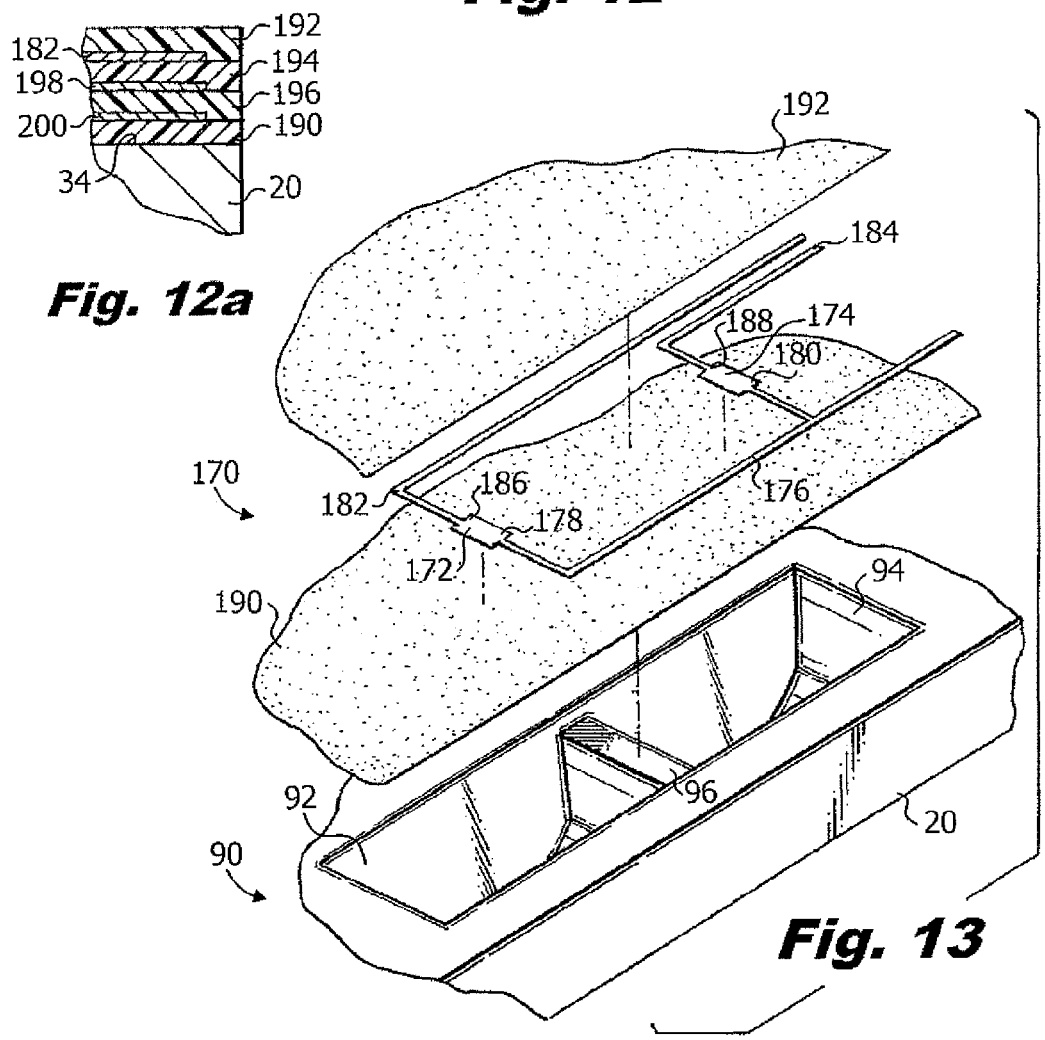
Fig. 12a
Fig. 13

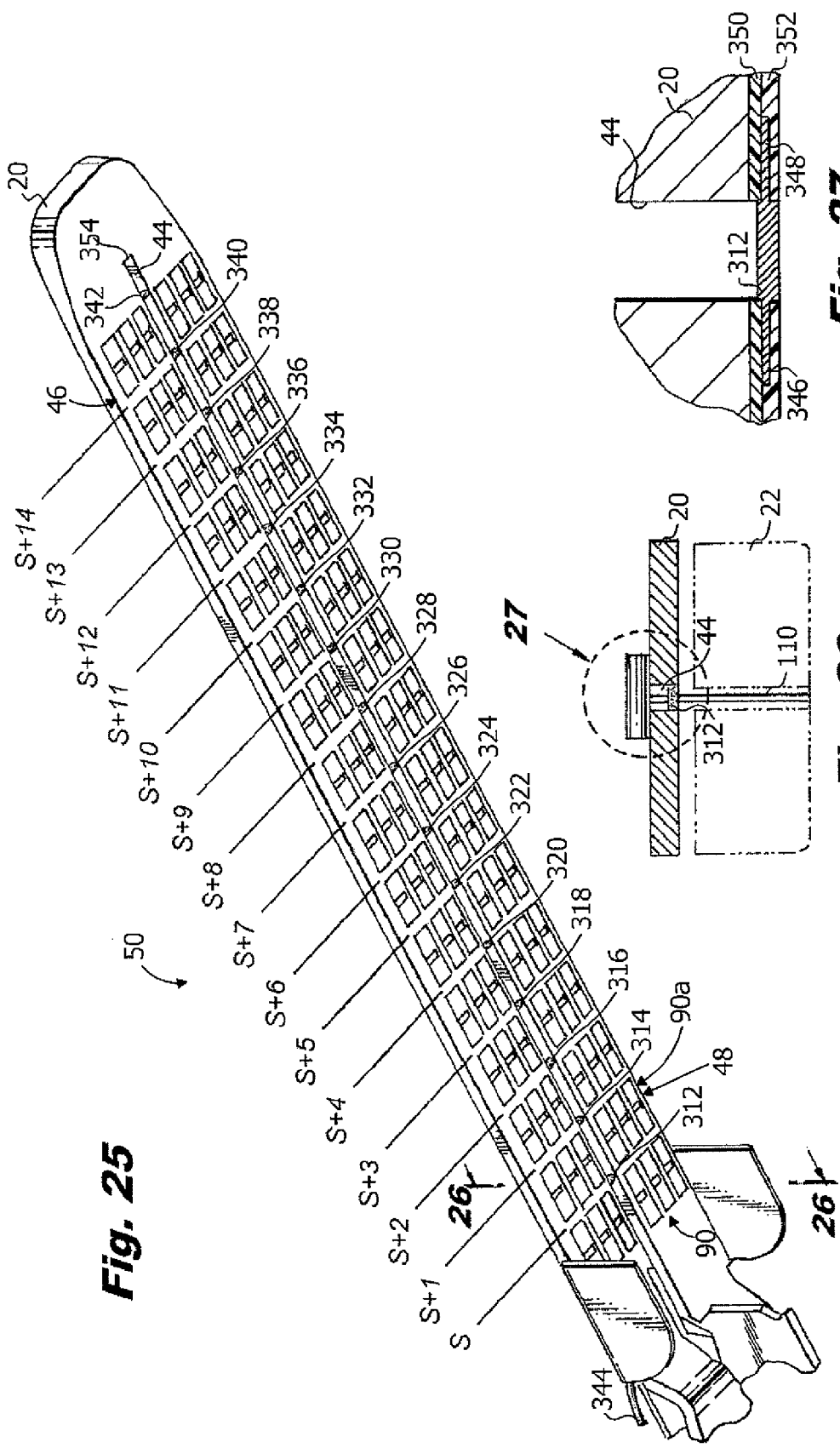

STAPLE FORMATION RECOGNITION FOR A SURGICAL DEVICE

CROSS REFERENCE TO RELATED APPLICATION

The present application claims the benefit of and priority to U.S. Provisional Application Ser. No. 61/580,753, filed on Dec. 28, 2011, the entire contents of which are incorporated herein by reference.

BACKGROUND

1. Technical Field

The present disclosure relates to an anvil member incorporating a staple formation recognition system for use with a surgical stapling instrument. More particularly, the present disclosure relates to an anvil member having a series of electrical traces positioned within staple forming pockets of the anvil member which detect the correct or incorrect formation of legs of a surgical staple within the staple forming pockets.

2. Background of Related Art

During various surgical procedures it is necessary to staple tissue with a surgical stapling instrument or surgical stapler to connect tissue sections or close off ends of tubular tissue sections permanently or temporarily to prevent leakage or prior to reconnection with other tissues. Tissue to be stapled is clamped between a staple containing cartridge and an anvil member of the surgical stapler. Thereafter, the surgical staples are ejected from the staple containing cartridge and into the anvil member where they are crimped within staple crimping pockets formed in an underside of the anvil member.

Occasionally, staples may encounter bone or other tough tissues where they become deformed prior to crimping. Tissue penetrating legs of the staples may become bent prior to entering the staple pockets or may become deflected or skewed aside resulting in improper or incomplete staple formation. This may lead to inadvertent tissue separation or, in the case of tubular tissue sections, leakage contaminating the operative site. Additionally, it is common to follow the staples as they are being crimped through tissue with a knife blade to sever apart the stapled tissue sections. If the knife blade passes through a poorly formed staple line in the tissue, similar problems may occur.

Therefore, it is desirable to incorporate a staple formation recognition system into the anvil member of a surgical stapler. It is further desirable to incorporate a staple formation recognition system that can analyze the formation of the individual legs of the surgical staple separately. It is still further desirable to provide a staple formation recognition system that can track the progress of an individual staple leg as it passes through a staple pocket. It is yet still further desirable to incorporate a knife blade position indication system to track the progress of the knife blade relative to a staple line being formed.

SUMMARY

There is disclosed a staple formation recognition system for use with an anvil member of a surgical stapler. The system generally includes an anvil member, defining a staple crimping pocket system having first and second staple pockets, and a trace system at least partially extending within the staple crimping pocket system. A controller electrically is connected to the trace system for detecting a condition of the trace system indicative of proper or improper formation of a surgical staple within the staple crimping pocket system. The trace system includes a first trace pad extending across the first staple pocket of the staple crimping pocket system.

In one embodiment, the trace system and the controller form an open electrical circuit and a surgical staple completes the electrical circuit when the surgical staple is properly formed in the staple crimping pocket system.

In a specific embodiment, the trace system includes a second trace pad extending across the second staple pocket of the staple crimping pocket system such that a properly formed surgical staple completes the electrical circuit when in contact with the first and second trace pads.

An electrically resistive layer is positioned between the trace system and anvil member to the electrically isolate the trace system from the anvil member. An electrically resistive layer is also applied over the trace system to electrically isolate the trace system from the environment.

In a particular embodiment, the anvil member forms a second trace pad for engagement with a leg of a surgical staple to complete the electrical circuit. In this embodiment, an electrically resistive layer is applied over the anvil member and the electrically resistive layer has a window to expose the anvil member to the leg of the surgical staple.

In an alternative embodiment, the trace system and the controller form a closed electrical circuit and a surgical staple interrupts the electrical circuit when the surgical staple is properly formed in the staple crimping pocket system.

In a more specific embodiment, the trace system includes a second trace pad extending across the second staple pocket of the staple crimping pocket system such that a properly formed surgical staple interrupts the electrical circuit when at least one of the first and second trace pads are broken by a leg of the staple.

In a particular embodiment, the trace system includes first and second conductive wires extending from opposed ends of the first trace pad and the trace system is electrically isolated from the anvil member by an electrically resistive layer.

In an alternative particular embodiment, the trace system includes a first conductive wire extending from a first end of the first trace pad and a second end of the first trace pad forms an electrically conductive path to the anvil member through an opening in the electrically resistive layer.

In a more specific embodiment, one of the conductive wires forms a common electrical path with one end of a second trace pad in the second staple pocket.

In a still more specific embodiment, the trace system includes multiple trace pads extending across the first staple pocket to track the formation of the leg of the surgical staple as it passes through the first staple pocket.

In at least some embodiments, at least a portion of the trace system is adhered to at least a portion of the anvil member. In at least some embodiments at least a portion of the trace system is adhered to at least a portion of the anvil member by an adherence method selected from the group consisting of printing, etching, electrolyzing, electron beam applicating, photolithographing, spraying, or any combination thereof.

In at least some embodiments, the controller is further configured to detect a sequence of staple formation and qualities of individual staple formations and compare the sequence of staple formation and qualities of the individual staple formations to a predetermined sequence/array of qualities to determine at least one probability of a staple line failure.

In at least some embodiments, the controller reads one or more properties of the trace system including resistance, inductance, impedance, or capacitance.

In at least some embodiments, the controller is further configured to detect the relative position of a blade and compare the detected position with a sequence of staple formation to ensure that stapling and cutting is occurring within a predetermined tolerance.

In at least some embodiments, further comprising a plurality of trace systems disposed upon each other, each being electrically insulated from each other by a resistive layer disposed between each trace system.

In at least some embodiments, the first trace pad may be flat or shaped to follow a curvature of at least one of the staple pockets.

There is also disclosed a method of detecting the proper formation of legs of a surgical staple with a staple pocket of an anvil member. The method includes providing an anvil member having first and second staple crimping pockets and a staple formation recognition system including a trace pad extending across the first staple crimping pocket and in electrical communication with a controller. The method includes engaging the trace pad with a leg of a surgical staple.

In one embodiment, the trace pad is engaged by connective contact with the surgical staple while in an alternative embodiment, wherein the trace pad is engaged by being severed by the surgical staple.

In at least some embodiments, the method further includes detecting a sequence of staple formation and qualities of individual staple formations and comparing the sequence of staple formation and qualities of individual staple formations to a predetermined sequence and array of qualities to determine a probability of a staple line failure.

There is further disclosed a knife blade position system for use in an anvil member of a surgical stapler. The knife blade position system generally includes a trace pad positioned within a knife slot formed within an anvil member and a controller electrically connected to the trace pad such that the trace pad and controller form a complete electric circuit. The trace pad is positioned between successive staple crimping pocket systems formed in an underside of the anvil member and is broken by movement of the knife blade through the trace pad to track the progress of the knife blade relative to the staple crimping pocket systems.

DESCRIPTION OF THE DRAWINGS

Various embodiments of the presently disclosed staple formation recognition system for use with a surgical stapler are disclosed herein with reference to the drawings, wherein:

FIG. 6 is a perspective view, with parts separated, of one embodiment of a staple trace system and a staple crimping pocket system of the anvil member;

FIG. 7 is a perspective view, partially shown in section, of the staple trace system and staple crimping pocket system of FIG. 6;

FIG. 8 is a side view, partially shown in section, of a surgical staple being formed within the staple crimping pocket system of the anvil and contacting trace pads of the staple trace system;

FIG. 12 is a partial top plan view of an alternative embodiment of a staple trace system;

FIG. 12a is a cross-sectional view taken along lines 12a-12a of FIG. 12;

FIG. 13 is a perspective view, with parts separated, of the staple trace system and a staple crimping pocket system of an anvil member of FIG. 12;

FIG. 25 is a perspective view of an anvil member incorporating a knife position trace system;

FIG. 26 is a cross-sectional view taken along lines 26-26 of FIG. 25; and

FIG. 27 is an enlarged area of detail view of FIG. 26.

DETAILED DESCRIPTION OF EMBODIMENTS

Embodiments of the presently disclosed staple formation recognition systems will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
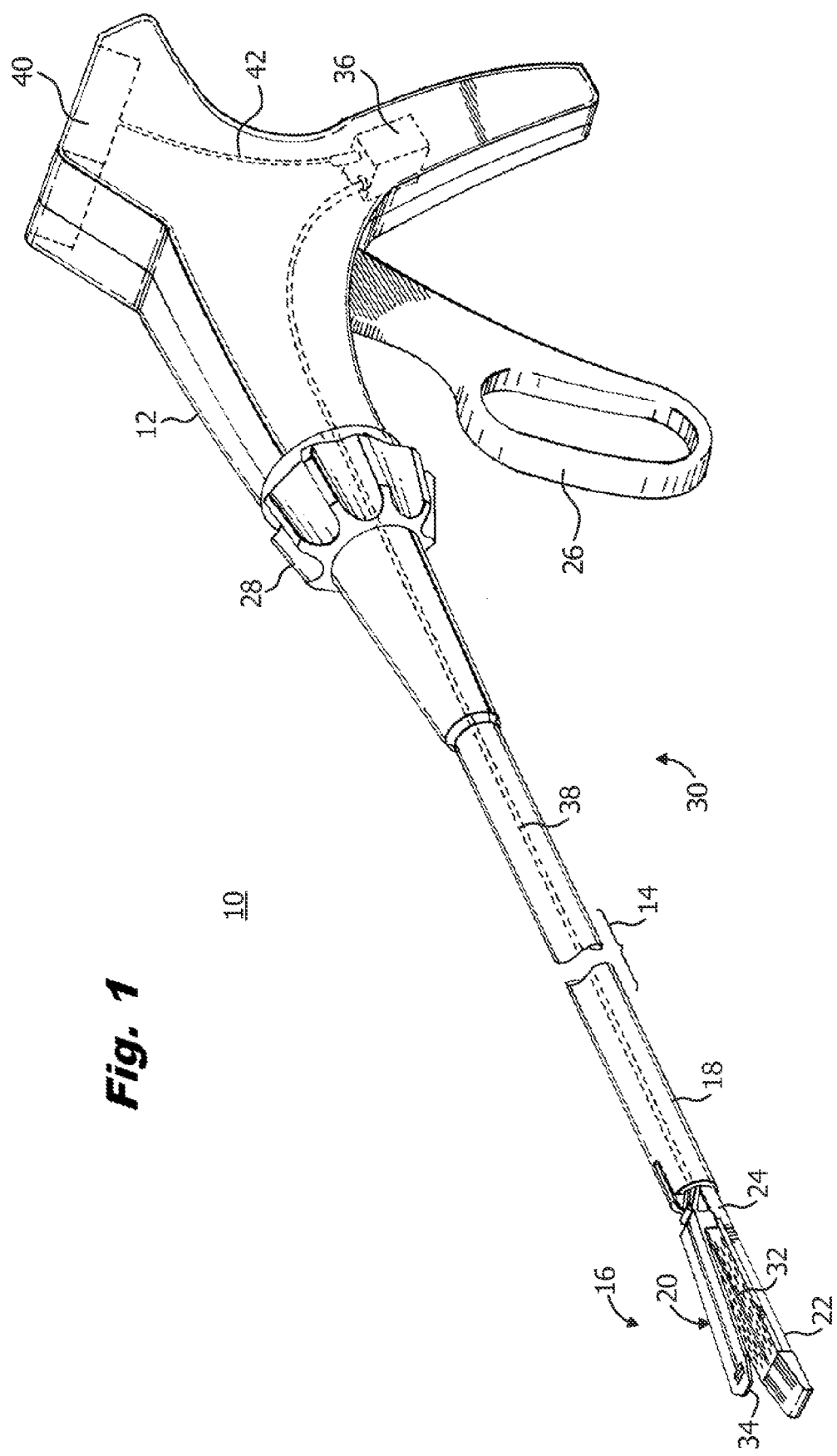
FIG. 1 is a perspective view of a surgical stapler incorporating on embodiment of a staple formation recognition system.

Referring initially to FIG. 1, there is disclosed a surgical stapler 10 having a handle portion 12 and an elongate tubular member 14 extending distally from handle portion 12. An end effector 16 is mounted on a distal end 18 of elongate tubular member 14 and generally includes an anvil member 20 and a staple cartridge 22. A proximal end 24 of staple cartridge 22 is removably attached to distal end 18 of elongate tubular member 14. Anvil member 20 is movably mounted relative to staple cartridge 22 such that anvil member 20 is movable from an open position spaced from staple cartridge 22 to a closed position substantially adjacent to and in operative alignment with staple cartridge 22. A trigger 26 is provided on handle portion 12 to move anvil member 20 between the open and closed positions relative to staple cartridge 22. A rotation knob 28 is rotatably mounted on handle portion 12 and is affixed to elongate tubular member 14. Rotation of rotation knob 28 relative to handle portion 12 functions to rotate and orient end effector 16 relative to tissue being operated upon.

Surgical stapler 10 incorporates a novel staple formation recognition system 30 which is provided to evaluate the accuracy of the formation of a surgical staple (not shown) driven from staple cartridge 22 and into anvil member 20. Staple formation recognition system 30 includes a staple formation recognition or trace system 32 which is provided on an underside 34 of anvil member 20. Staple formation recognition system 30 additionally includes a computer module, controller, or CPU 36 provided within a handle portion 12 and which receives and evaluates data received from staple trace system 32 and transmits the results in various forms to a display screen 40 provided on handle portion 12. CPU 36 also includes the power to maintain or establish an electrical circuit within staple trace system 32. As shown, a first cable 38 extends between staple trace system 32 and CPU 36 and a second cable 42 is provided between CPU 36 and display screen 40.

Figure 2:
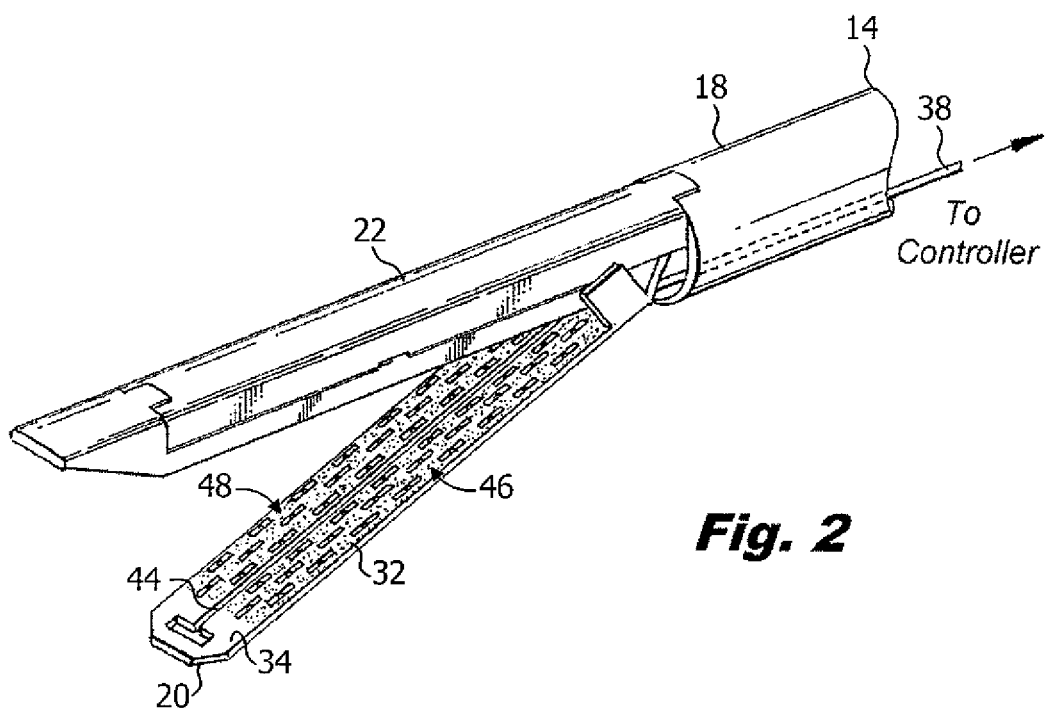
FIG. 2 is a perspective view of the distal end of the surgical stapler including an anvil member incorporating one embodiment of a staple formation recognition system.

Referring for the moment to FIG. 2, anvil member 20 generally includes a longitudinally extending knife slot 44 and longitudinally extending series or multiple rows of staple crimping pockets 46 and 48 extending alongside knife slot 44. As noted hereinabove, staple trace systems 32 is provided on underside 34 of anvil member 20.

Figure 3:
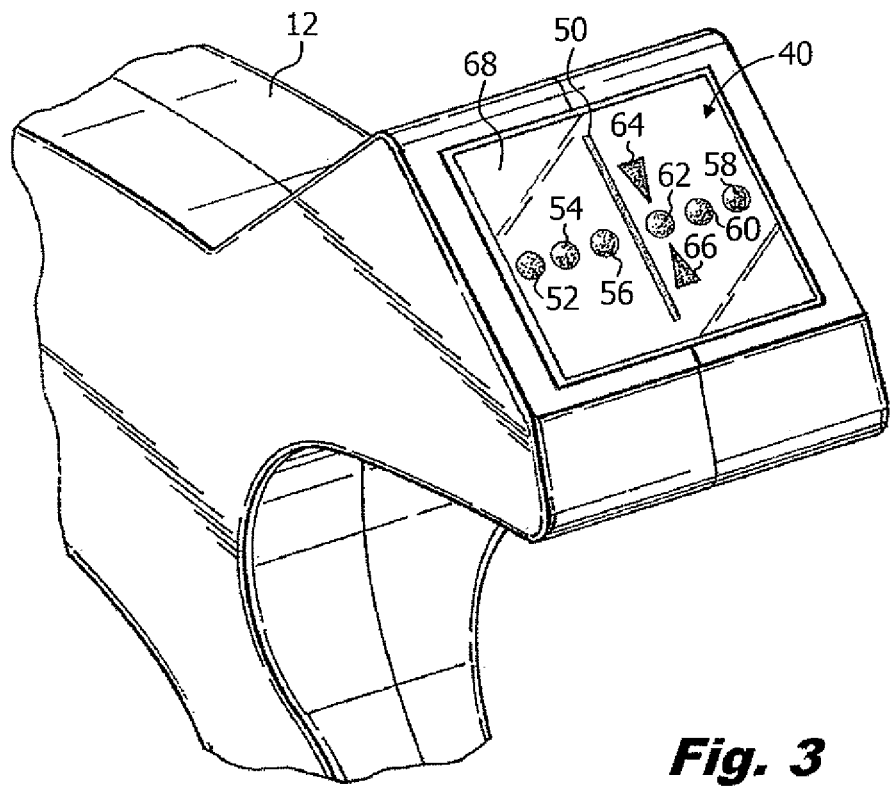
FIG. 3 is a perspective view of the proximal end of the surgical stapler including a display screen.

With reference to FIG. 3, display screen 40 is provided to illustrate to the surgeon the results of the data provided by staple trace systems 32 and as analyzed by CPU 36. This data may take various forms such as, for example, the correct or incorrect formation of crimped legs associated with individual staples, rows of staples, staples positioned side-by-side, etc. Additionally, data regarding the current position of a knife blade (not shown) associated with staple cartridge 22 may also be provided on display screen 40. For example, display screen 40 includes an elongate knife position indicator 50. Outer, center, and inner staple formation indicators 52, 54 and 56, respectively, are provided on one side of knife position indicator 50 and correspond to multiple rows of staple crimping pockets 46 (FIG. 2). Similarly, outer, center and inner staple formation indicators 58, 60 and 62, respectively, are located on an opposite side of knife position indicator 50 and correspond to multiple rows of staple crimping pockets 48. In order to indicate whether a particular leg of an associated staple has been correctly or incorrectly formed, display screen 40 additionally includes leg confirmation arrows 64 and 66 which are provided to indicate which leg of a particular staple being formed in a particular staple pocket of anvil member 20 is being analyzed. Various colors (not depicted) may be used to indicate proper or improper staple line formation. For example, green may be associated with leg confirmation arrows 64 and 66 to indicate a correct staple leg formation while an alternate color such as, for example, red may be associated with leg confirmation arrows 64 and 66 to indicate an incorrect or incomplete crimping of the indicated staple leg.

It should be noted that provisions may be made within display screen 40 for indicating various or alternative types of data. Additionally display screen 40 may incorporate additional displays such as, for example, numerical displays, graphical displays, digital and/or analog displays, to convey to the surgeon data analyzed by CPU 36. Further, display screen 40 may incorporate a touch screen surface 68 to allow a surgeon to choose the types and amounts of data viewed and alternate between various data options. CPU 36 can provide an initial menu or list of data available to the surgeon which can then be chosen and preset depending upon the particular surgical procedure being performed and type of staple cartridge being utilized.

Figure 4:
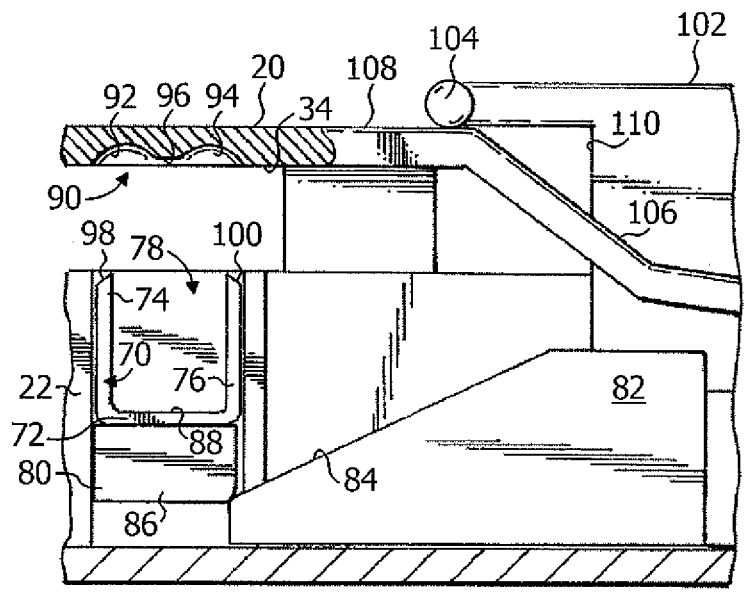
FIG. 4 is a side view, partially shown in section, of a staple cartridge and the anvil member of the surgical stapler of FIG. 1.

Referring now to FIG. 4, there is illustrated a surgical staple 70 provided within staple cartridge 22. Surgical staple 70 generally includes a backspan 72 having first and second tissue penetrating legs 74 and 76 extending from backspan 72. Surgical staple 70 is initially contained within a staple pocket 78 formed within staple cartridge 22. A pusher 80 is provided within staple pocket 78 and is located beneath surgical staple 70. Pusher 80 is provided to eject surgical staple 70 out of staple pocket 78 and drive surgical staple 70 into underside 34 of anvil member 20. In order to move pusher 80 upwardly within staple pocket 78, staple cartridge 22 additionally includes a drive bar 82 having an angled face 84, which engages an undersurface 86 of pusher 80. As drive bar 82 is driven distally through staple cartridge 22, angled face 84 causes an upper surface 88 of pusher 80 to engage backspan 72 of surgical staple 70 thereby driving surgical staple 70 upwardly and out of staple pocket 78.

Figure 5:
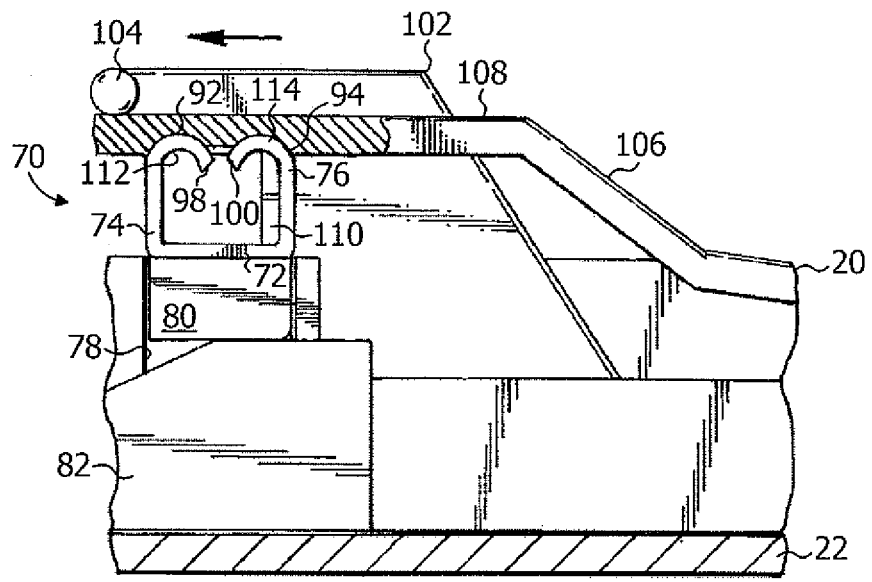
FIG. 5 is a side view, partially shown in section, of the surgical staple being driven out of the staple cartridge and formed against an underside of the anvil member.

Referring now to FIGS. 4 and 5, the formation of surgical staple 70 within a staple crimping pocket system 90 formed in underside 34 of anvil member 20 will now be described. Staple crimping pocket system 90 generally includes a plurality of first and second staple crimping pockets 92 and 94, respectively, and a central ridge 96 located between first and second staple crimping pockets 92 and 94. First and second staple crimping pockets 92 and 94 are configured to receive and bend tissue penetrating tips 98 and 100 of first and second legs 74 and 76, respectively, of surgical staple 70.

Initially, with regard to FIG. 4, surgical staple 70 is positioned within staple pocket 78 and staple cartridge 22 and above pusher 80. Drive bar 82 is in a retracted or proximal most initial position. Referring for the moment initially to FIG. 1, trigger 26 is actuated to move anvil member 20 between the open position to the closed position relative to staple cartridge 22 and eject surgical staples 70 out of staple pocket 78. Returning to FIG. 4, as trigger 26 is actuated, an I-beam 102 is driven distally over anvil member 20. Specifically, a crossbar 104 of I-beam 102 engages and rides up along an angled proximal end 106 of anvil member 20 to move anvil member 20 from the open to closed position relative to staple cartridge 22. Crossbar 104 continues to move along an upper surface 108 of anvil member 20 to maintain anvil member 20 in the closed position relative to staple cartridge 22. Moving anvil member 22 the closed position locates first and second staple crimping pockets 92 and 94 directly above tissue penetrating tips 98 and 100 of surgical staple 70. It should be noted that, I-beam 102 additionally includes a distally facing knife blade 110 which is configured to pass through knife slot 44 in staple cartridge 22 and tissue (not shown) and sever the tissue between multiple rows of staple crimping pockets 46 and 48 (See FIG. 2).

Referring now to FIG. 5, as trigger 26 continues to be actuated, drive bar 82 is moved distally causing angled face 84 to engage undersurface 86 of pusher 80. This moves pusher 80 upwardly within staple pocket 78 driving surgical staples 70 out of staple pocket 78. At surgical staple 70 is driven upwardly by pusher 80, tissue penetrating tips 98 and 100 of first and second legs 74 and 76 enter and are bent within first and second staple crimping pockets 92 and 94 of staple crimping pocket system 90 thereby bending tissue penetrating tips 98 and 100 and curved crimped leg portions 112 and 114 of first and second legs 74 and 76, respectively, back upon themselves to secure together tissue captured between anvil member 20 and staple cartridge 22 (not shown). In this manner, surgical staple 70 is driven out of staple pocket 78 in staple cartridge 22 and formed within staple crimping pocket system 90 in anvil member 20.

Turning now to FIGS. 6-8, there is disclosed one embodiment of a staple formation recognition or trace system 120 for use in staple crimping pocket system 90 of anvil member 20. Staple trace system 120 is provided to detect the proper or improper formation of surgical staple 70 within staple crimping pocket system 90 and, in conjunction with CPU 36, enable that data to be reflected on display system 40 (FIG. 2). In this embodiment, surgical staple 70 is formed from a conductive material, such as, for example, stainless steel and forms part of an electrical circuit with staple trace system 120, CPU 36 and display system 40.

Referring initially to FIGS. 6 and 8, staple trace system 120 generally includes a first contact member or trace pad 122 and a second contact member or trace pad 124. First and second trace pads 122 and 124 are formed from a conductive material such as, for example, stainless steel, copper, etc. A first conductive wire 126 extends from first trace pad 122, through first cable 38 (FIG. 2), and electrically connects first trace pad 122 to CPU 36. Similarly, a second conductive wire 128 extends from second trace pad 124, through first cable 38, and electrically connects second trace pad 124 to CPU 36. When first and second trace pad 122 and 124 are engaged by properly formed legs of surgical staple 70, surgical staple 70 completes an electrical circuit with first and second trace pads 122 and 124 and CPU 36.

In order to electrically isolate anvil member 20 from first and second trace pads 122 and 124, as well as first and second conductive wires 126 and 128, staple trace system 120 additionally includes a first thin, electrically resistive layer or coating 130 applied over the length of anvil member 20. Furthermore, in order to prevent inadvertent electrical conduction between first and second trace pads 122 and 124, staple trace system 120 further includes a second thin, electrically resistive layer or coating 132 applied over first and second trace pads 122 and 124 and first and second conductive wires 126 and 128 along the length of anvil member 20. As specifically shown in FIG. 7, first and second trace pads 122 and 124 extend across bottoms 134 and 136 of respective first and second staple crimping pockets 92 and 94. While this embodiment is being described with respect to a particular staple crimping pocket system 90, it should be noted that multiple sequential arrays of staple trace systems 120 are applied over all staple crimping pocket systems 90 located along the length of anvil member 20.

Staple trace system 120 may be formed on anvil member 20 as separate components, or, alternatively, staple trace system 120 may be applied to anvil member 20 as multiple arrays of staple trace system 120 by layering the materials through various known application methods. For example, the sequential arrays of first and second staple trace pads 122 and 124 along with first and second conductive wires 126 and 128 are applied, printed, etched, electrolyzed, electron beam applied, photolithographed, sprayed, or adhered over first electrically resistive coating 130. Subsequently, second electrically resistive coating 132 is then applied over first and second trace pads 122 and 124 and first and second conductive wires 126 and 128.

Referring now to FIGS. 4, 5 and 7-8, the use of staple trace system 120 to detect correctly formed staple within staple crimping pocket system 90 will now be described. Initially, surgical staple 10 is actuated to drive pusher 80 upwardly within staple pocket 78 forcing surgical staple 70 toward anvil member 20 and into staple crimping pocket system 90 in the manner described herein above. Referring now to FIG. 8, as tissue penetrating tips 98 and 100 of first and second legs 74 and 76 enter first and second staple crimping pockets 92 and 94, tissue penetrating tips 98 and 100 initially engage respective outer or side edges 138 and 140 of first and second staple crimping pockets 92 and 94. Tissue penetrating tips 98 and 100 pass over bottoms 134 and 136 and up respective inner edges 142 and 144 of first and second staple crimping pockets 92 and 94 toward central ridge 96. When surgical staple 70 has been fully and correctly formed, it results being a classic "B" shaped surgical staple 146.

As tissue penetrating tips 98 and 100 enter first and second staple crimping pockets 92 and 94, tissue penetrating tips 98 and 100 scratch, break, penetrate, or otherwise pass through second resistive layer or coating 132 causing curved crimped leg portions 112 and 114 to engage corresponding first and second trace pads 122 and 124 thereby completing electrical circuit with CPU 36 and conveying that information to display screen 40. This informs the surgeon that surgical staple 146 has been correctly and fully formed within a particular staple crimping pocket system 90. As noted here in above, staple trace system 120 is present in all the staple crimping pocket systems 90 associated with anvil member 20 and the process is repeated within each staple crimping pocket system 90 so that the surgeon can confirm each surgical staple 70 is properly formed and the surgical staple line across the subject tissue is proper.

It should be noted that in the event tissue penetrating tips 98 and/or 100 engage tough tissue and/or bone, tissue penetrating tips 98 and 100 may not sufficiently pass through second resistive layer or coating 132 such that one or both of leg portions 112 or 114 of surgical staple 70 does not contact a corresponding first or second staple trace pad 122 and 124 and/or does not complete the electrical circuit with CPU 36. This information is also relayed to the surgeon via screen 40 so that the surgeon may stop the surgical procedure and take corrective measures.

Figure 9:
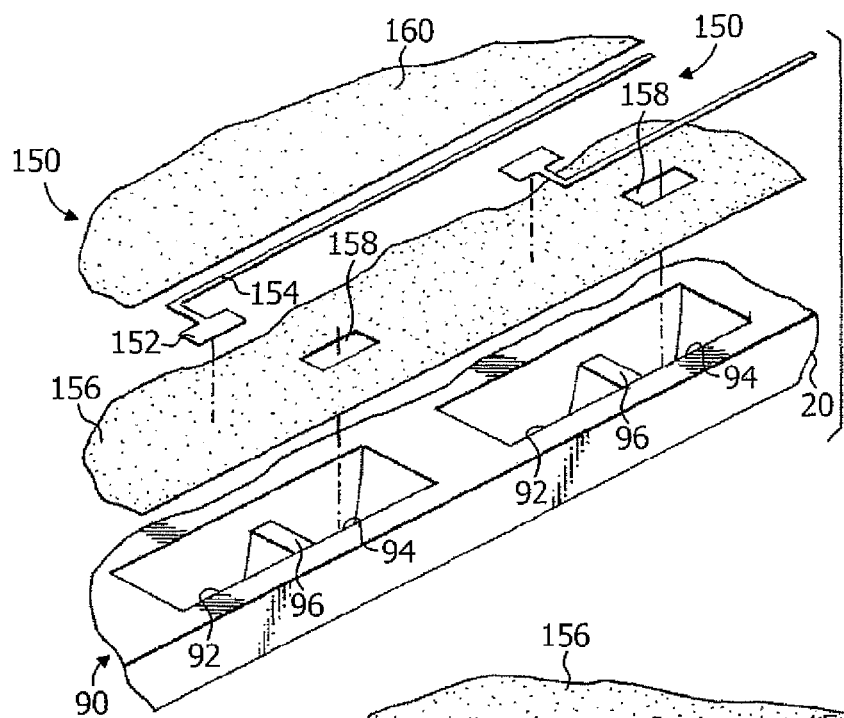
FIG. 9 is a perspective view, with parts separated, of an alternative embodiment of a staple trace system and a staple crimping pocket system.
Figure 10:
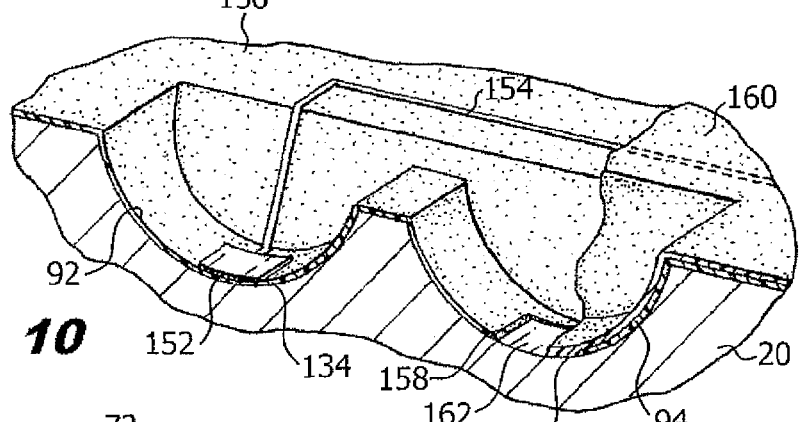
FIG. 10 is a side view, partially shown in section, of the staple trace system and staple crimping pocket system of FIG. 9.
Figure 11:
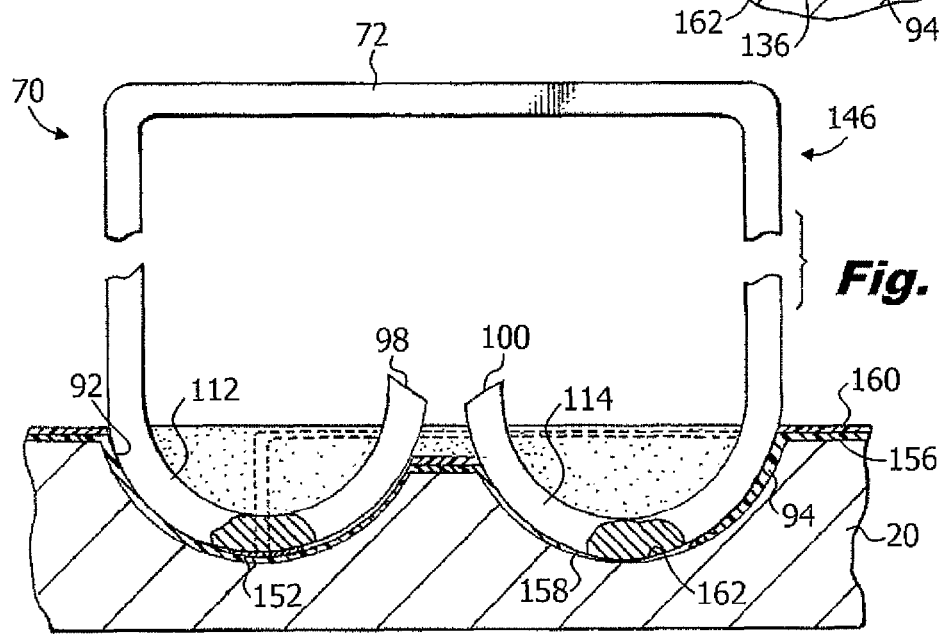
FIG. 11 is a side view, partially shown in section, of a surgical staple being formed within the staple crimping pocket system of the anvil and contacting a trace pad of the staple trace system of FIG. 9 and a portion of the anvil member within the staple crimping pocket system.

Referring now to FIGS. 9-11, there is disclosed an alternative embodiment of a staple formation recognition or trace system 150 for use with anvil member 20. Referring initially to FIGS. 9 and 10, staple trace system 150 uses anvil 20 as a common ground or return to CPU 36 to complete the electrical circuit. Staple trace systems 150 are illustrated in FIG. 9 for multiple staple crimping pocket systems 90 and generally includes a staple contact member or trace pad 152 having a conductive wire 154 which extends back to CPU 36. A first resistive layer or coating 156 is applied over anvil member 20 and includes a window 158 exposing anvil member 20. A second resistive layer or coating 158 is applied over staple trace pad 152 and conductive wire 154 and covers window 160 in first electrically resistive layer or coating 156. With specific reference to FIG. 10, staple trace pad 152 and window 158 in first restive layer or coating 156 are positioned within bottoms 134 and 136 of first and second staple crimping pockets 92 and 94. Window 158 in first resistive layer or coating 156 exposes a contact patch 162 of anvil member 20 (FIG. 10).

In use, surgical staple 70 is ejected out of staple containing cartridge 22 and into anvil member 20 in the manner described herein above. With reference to FIG. 11, as tissue penetrating tips 90 and 100 enter first and second staple crimping pockets 92 and 94, tissue penetrating tips 90 and 100 pass through second resistive layer or coating 160 causing curved leg portion 112 to engage trace pad 152 and second curved leg portion 114 to engage contact patch 162 of anvil member 20 through window 158 in first resistive layer or coating 156. This allows the now fully formed surgical staple 146 to complete the electrical circuit with CPU 36 and convey that information to the surgeon. As with the prior embodiment, should first or second tissue penetrating tips 98 or 100 engage bone or other tough tissue's such that surgical staple 70 is not properly formed, one of first and second leg portions 112 and 114 do not contact respective trace pad 152 or contact patch 162 leaving the electrical circuit open and conveying that information to the surgeon via display screen 40.

Referring to FIGS. 12-15, there is disclosed an alternative staple formation recognition or trace system 170 for use with anvil member 20. In this, and the remaining embodiments, the disclosed staple trace system 170 forms a fully complete electrical circuit with CPU 36. The detection of a fully and correctly formed surgical staple 70 is achieved by breaking the electrical circuit to create an open circuit and convey that information to the surgeon via display screen 40. In the event surgical staple contacts bone or other tough tissues or is otherwise not properly formed, the electrical circuit is not broken and that information is conveyed to the surgeon via display screen 40. As best shown in FIG. 12, multiple staple trace systems 170 are provided on anvil member 20 to cover multiple rows of staple crimping pockets 46.

Figure 14:
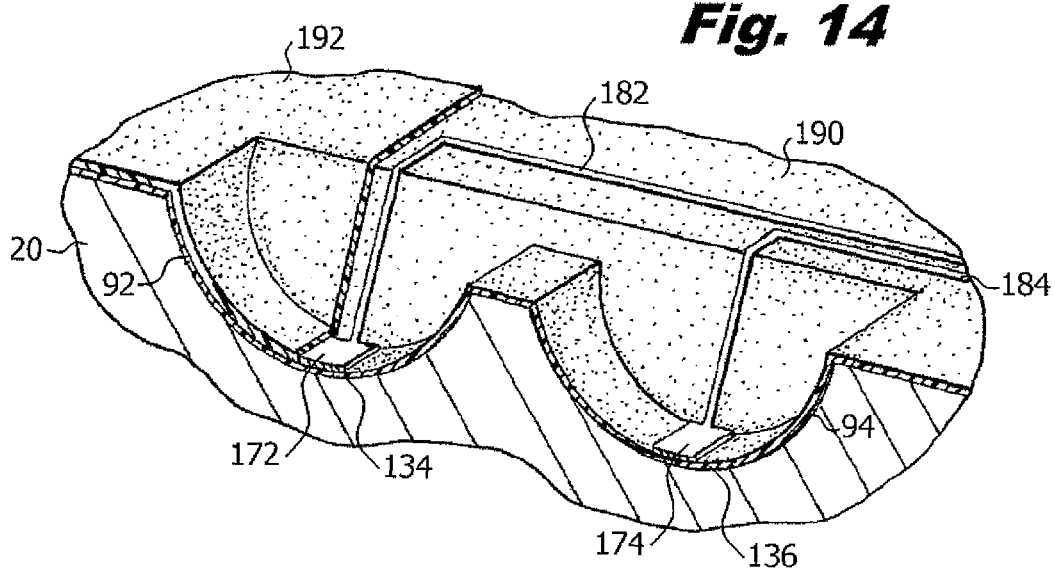
FIG. 14 is a side view, partially shown in section, of the staple trace system and anvil member of FIG. 12.

Referring to FIGS. 13-14, staple trace system 170 generally includes first and second contact or trace pads 172 and 174 and a common ground wire 176 which extends from respective first sides 178 and 180 of first and second trace pads 172 and 174 and extends back to CPU 36. Individual first and second conductive wires 182 and 184 extend from respective second sides 186 and 188 of first and second trace pads 172 and 174 and also extend back to CPU 36 thereby allowing staple trace system 170 to form a complete electrical circuit with CPU 36. A first resistive layer or coating 190 is initially applied over anvil member 20 and a second resistive layer or coating 192 is applied over first and second trace pads 172 and 174 and common, first and second conductive wires 176, 182 and 184, respectively.

Referring back for the moment to FIG. 12a, as noted above, multiple staple trace systems 170 are provided on anvil member 20. In order to conserve space on anvil underside 34, staple trace systems are "layered up" on underside 34. For example, intermediate resistive layers or coatings 194 and 196 are formed over prior resistive layers to electrically isolate conductive wires, such as, for example, conductive wires 198, 200, etc. associated with subsequent staple trace systems 170 on anvil member 20.

Referring now to FIG. 14, staple trace pads 172 and 174 extend across respective bottoms 134 and 136 of first and second staple crimping pockets 92 and 94 of staple crimping pocket system 90 to detect the correct formation of surgical staple 70. In this, and in following embodiments, the disclosed trace pads, for example first and second trace pads 172 and 174 are formed from conductive yet breakable, frangible or otherwise severable materials so as to allow the electrical connection to be broken by a properly formed surgical staple 70.

Figure 15:
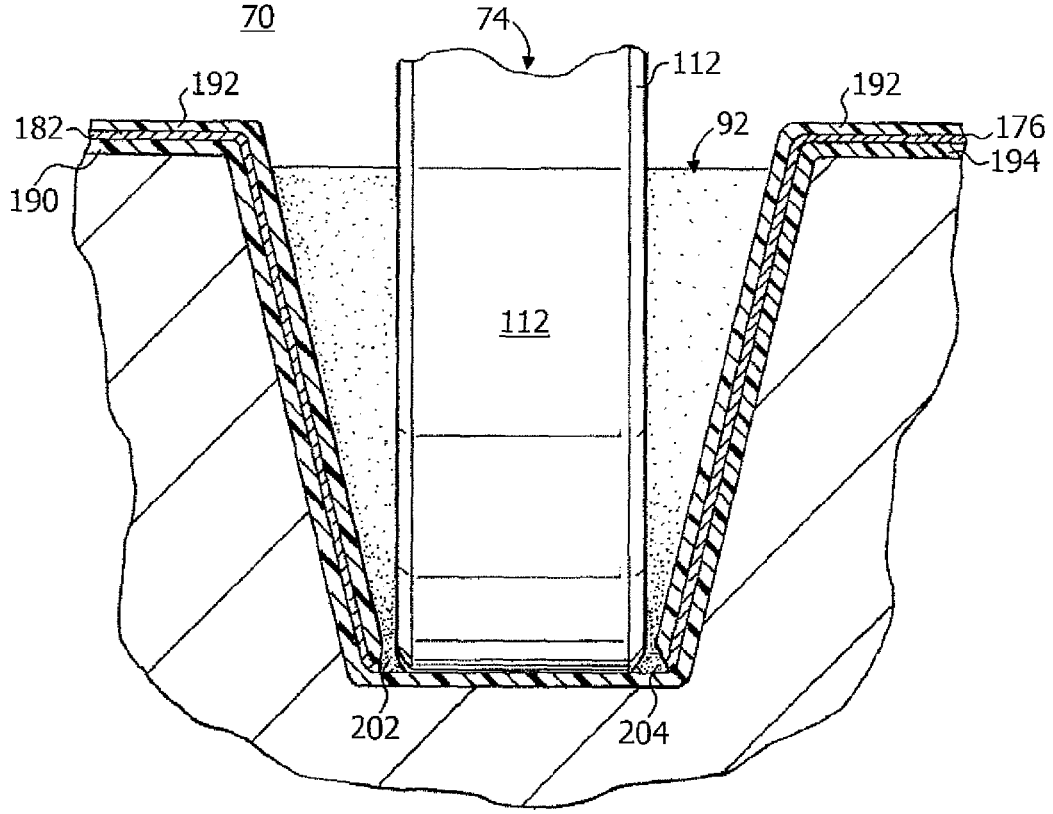
FIG. 15 is a cross-sectional view of one leg of the surgical staple breaking a trace pad of the staple trace system of FIG. 12.

With reference to FIG. 15, in use, as a leg of surgical staple 70 enters a staple crimping pocket, for example as leg 74 of surgical staple 70 enters staple crimping pocket 92, curved leg portion 112 is formed and breaks through second resistive layer or coating 192. If curved leg portion 112 is being properly formed, curved leg portion 112 also breaks or severs first trace pad 172 leaving broken or open ends 202 and 204 of first trace pad 172. This breaks or severs the electrical circuit with CPU 36 and that information is conveyed to the surgeon via display screen 40. In the event that curved leg portion 112 is not properly formed, first trace pad 172 is not broken or severed and the electrical circuit remains intact. CPU 36 maintains that condition illustrated on display screen 40 for the surgeon so that the surgical procedure may be stopped and corrective action taken.

Referring to FIGS. 16-19, there is disclosed yet another staple formation recognition or trace system 210 for use with anvil member 20. This embodiment is similar to that disclosed in FIGS. 9-11 hereinabove, in that staple trace system 210 utilizes the conductive material of anvil member 20 as a common ground or return to complete the electrical circuit with CPU 36. Similar to the previous embodiment, staple trace system 120 is an initially closed electrical circuit system and relies on the breaking of the electrical circuit to detect a properly formed surgical staple.

Figure 16:
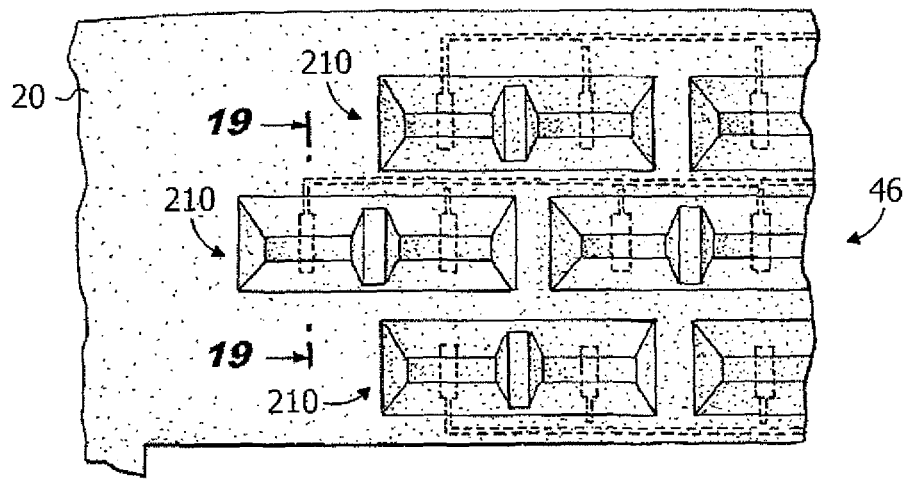
FIG. 16 is a partial top plan view of an alternative embodiment of a staple trace system.

However, unlike the prior embodiments which identified correct or incorrect formation of the entire surgical staple 70 regardless of which leg 72 and/or 74 was the source, staple trace system 210 specifically tests each leg 72 and 74 of surgical staple 70 separately and individually to identify which particular leg is improperly formed and convey that information to the surgeon on display screen 40. This allows the surgeon to better determine how to reposition surgical stapler 10 to avoid the problem area during stapling. As best shown in FIG. 16, multiple staple trace systems 210 are provided on anvil member 20 to cover multiple rows of staple crimping pockets 46.

Figure 17:
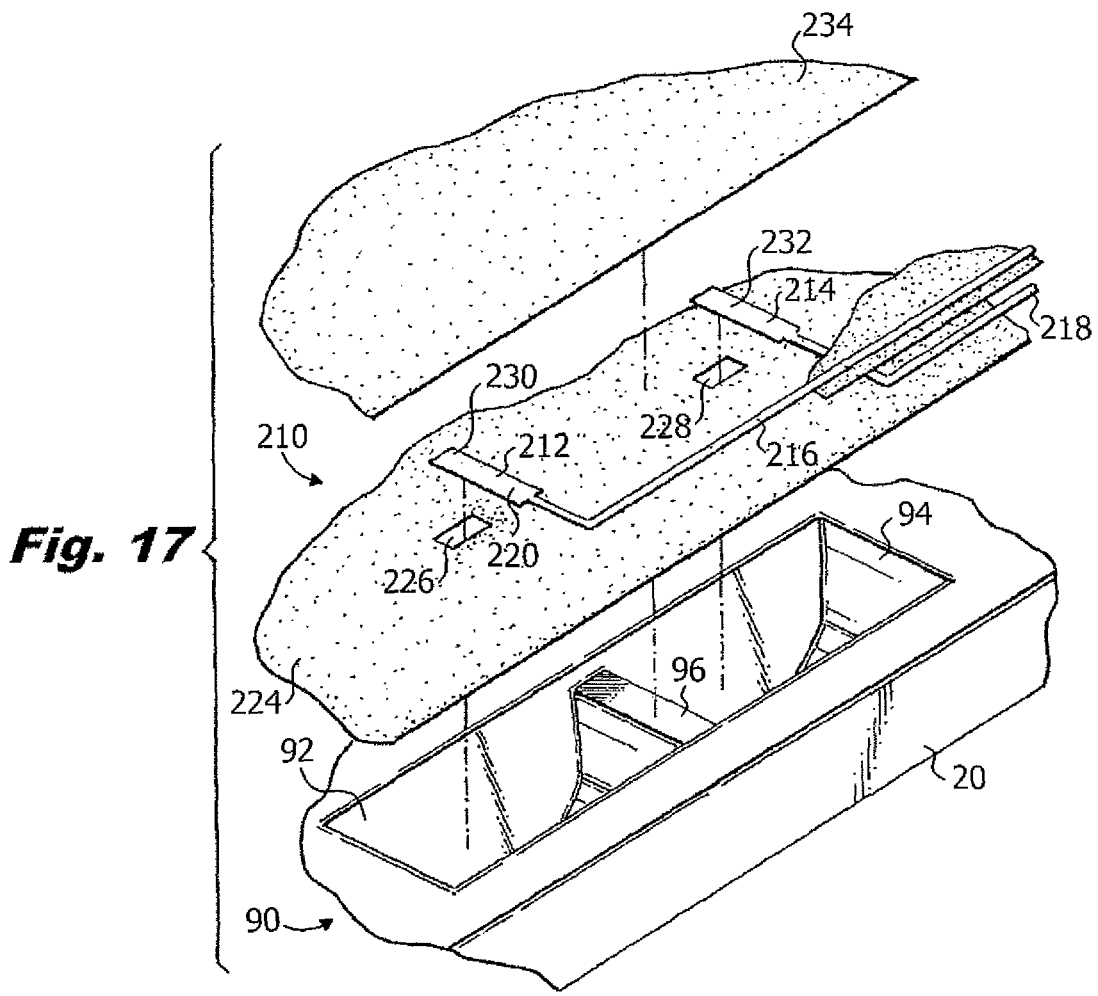
FIG. 17 is a perspective view, with parts separated, of the staple trace system of FIG. 16.

Referring now to FIG. 17, staple trace system 210 generally includes first and second staple trace pads 212 and 214 and first and second conductive wires 216 and 218. First staple trace pad 212 is located in staple pocket 92 of staple crimping pocket system 90 and second staple trace pad 214 is located in staple pocket 94 of staple crimping pocket system 90. First staple trace pad 212 and first conductive wire 216 form a complete electrical circuit with CPU 36. Second staple trace pad 214 and second conductive wire 218 form a separate and independent electrical circuit with CPU 36 so that each leg 72 and 74 of surgical staple 70 are tested separately within staple crimping pockets 92 and 94 for proper formation.

First conductive wire 216 extends from a first side 220 of first trace pad 212 and second conductive wire extends from a first side 222 of second trace pad 214. A first resistive layer or coating 224 is initially applied over anvil member 20 and includes first and second windows 226 and 228 located within, and offset from the centers of, staple pockets 92 and 94. A second end 230 of first trace pad 212 is in electrical contact with anvil member 20 through first window 226 and a second end 232 of second trace pad 214 is in electrical contact with anvil member 20 through second window 228. As noted above, anvil member 20 provides a common ground or return path for the electrical circuits with CPU 36. Finally, a second resistive layer or coating 234 is provided over first and second trace pads 212, 214 and first and second conductive wires 216 and 218 to electrically isolate them from their surroundings.

Figure 18:
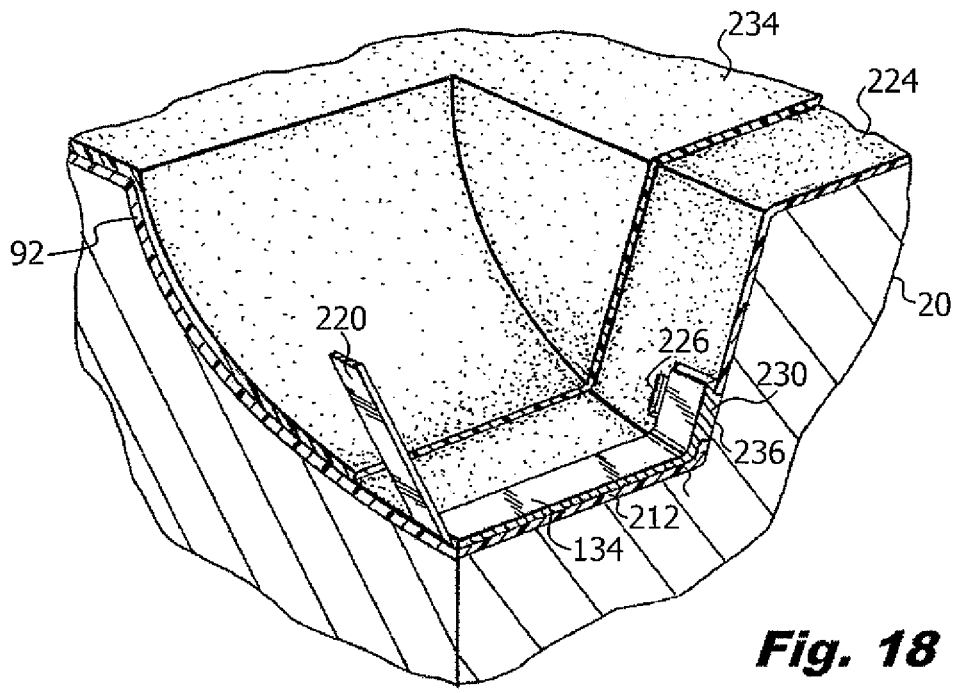
FIG. 18 is a perspective view, partially shown in section, only portion of the staple trace system of FIG. 17.

As best shown in FIG. 18, second end 230 of first trace pad 212 forms a contact patch 236 with anvil member 20 offset from bottom 134 of staple pocket 92. This leaves first trace pad 212 spanning bottom 134 of staple pocket 92. While not specifically shown, second end 232 of second trace pad 214 also form a contact patch with anvil member 20 offset from bottom 136 of second staple pocket 94 resulting in second trace pad 214 spanning bottom 136.

Figure 19:
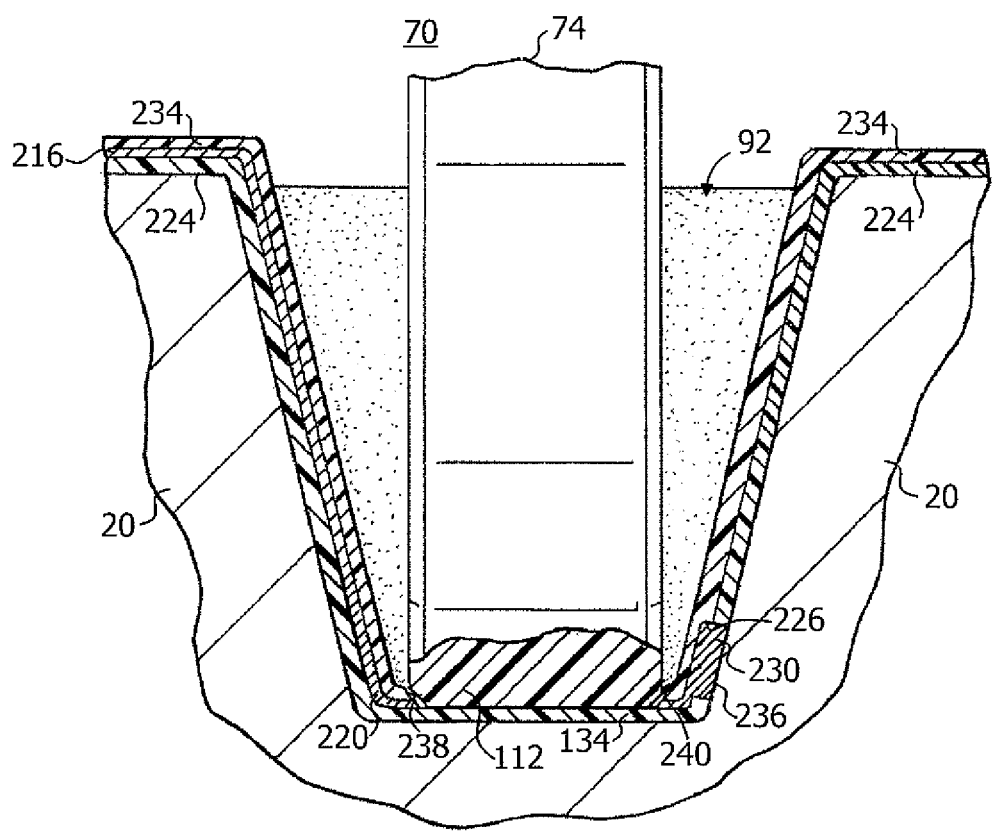
FIG. 19 is a cross-sectional view of one leg of the surgical staple breaking a trace pad of the staple trace system of FIG. 17.
Figure 20:
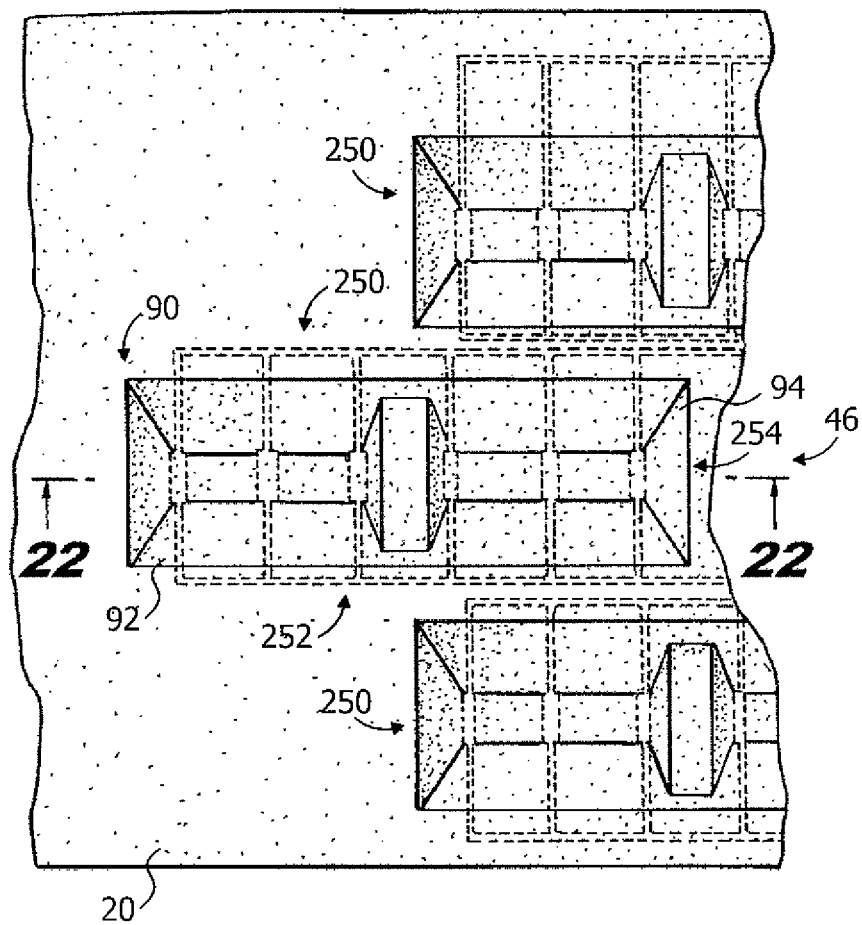
FIG. 20 is a partial top plan view of an alternative embodiment of a staple trace system.

Turning now to FIG. 19, in use, a leg of surgical staple 70, for example leg 74, a staple pocket, such as staple pocket 92. As surgical staple 70 is properly formed in staple crimping pocket system 90, curved crimped leg portion 112 of leg 74 penetrates second resistive coating or layer 234 and breaks or severs first trace pad 212 in bottom 134 of staple pocket 92. This leaves broken or severed ends 238 and 240 of first trace pad 212 separate and electrically isolated from each other breaking the electrical circuit with CPU 36. When first trace pad 212 is broken, indicating a properly formed staple leg 74, CPU 36 transmits that information to be displayed on display 40. In the event that staple leg 74 is not properly formed or does not sever first trace pad 212, the electrical circuit is not broken and that also is conveyed to the surgeon on display 40. The same situations are simultaneously repeated with second leg 76 of surgical staple 70 in staple pocket 94 with second trace pad 214.

Thus, staple trace system 210 is capable of analyzing the proper or improper formation of staple legs 74 and 76 separately and independently allowing the surgeon to confirm proper staple formation in that staple crimping pocket system 90 or take corrective action.

Turning now to FIGS. 20-24, there is disclosed a further staple formation recognition or trace system 250 which is designed to more precisely determine not only the proper or improper formation of staple legs 74 and 76 but, also, more specifically where along curved crimped leg portions 112 and 114 a problem may be occurring. Like the previous embodiment, each of the following traces form a complete electric circuit with CPU 36 and give an indication of proper formation when the respective circuits are broken or interrupted. Staple trace system 250 includes a first staple trace array 252 located in staple pocket 92 of staple crimping pocket system 90 and a second staple trace array 254 located in staple pocket 94 of staple crimping pocket system 90.

Figure 21:
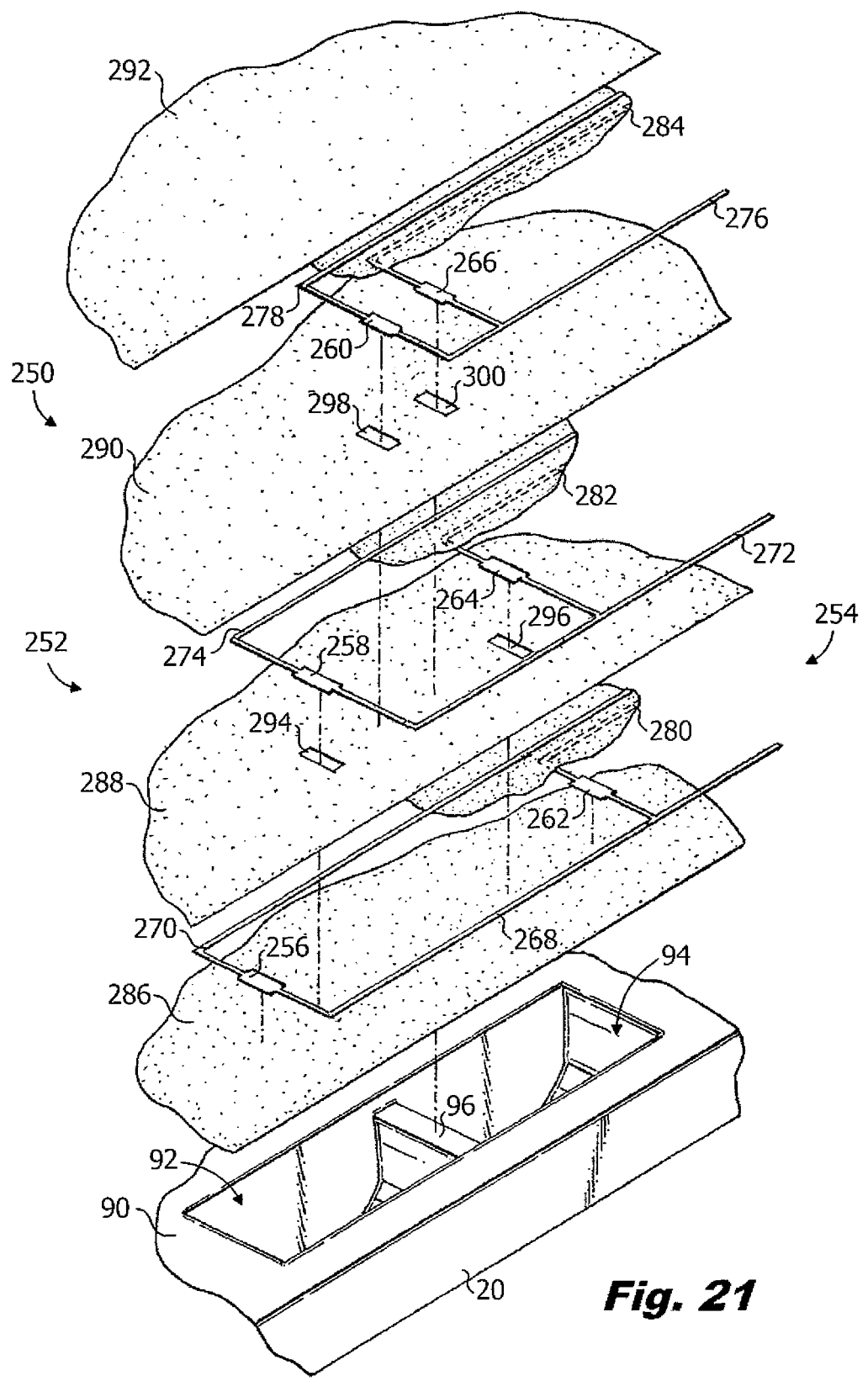
FIG. 21 is a perspective view, with parts separated, of the staple trace system of FIG. 20.

Referring to FIG. 21, first staple trace array 252 includes an outer trace pad 256, a center trace pad 258 and an inner trace pad 260. Likewise, second staple trace array 254 includes an outer trace pad 262, a center trace pad 264 and an inner trace pad 266. First staple trace array further includes a first common conductive wire 268 and a first conductive wire 270 extend from outer trace pad 256 and forms a complete electrical circuit with CPU 36. A second common conductive wire 272 and a second conductive wire 274 extend from center trace pad 258 to form a complete electrical circuit with CPU 36 and a third common conductive wire 276 and a third conductive wire 278 extend from inner trace pad 260 to form a complete electrical circuit with CPU 36.

Second staple trace array 254 shares first, second and third common conductive wires 268, 272 and 276 with first staple trace array 252 which extend from outer trace pad 262, center trace pad 264 and inner trace pad 266, respectively. Second staple trace array 254 further includes a fourth conductive wire 280 extending from outer trace pad 262, a fifth conductive wire 282 extending from center trace pad 264 and a sixth conductive wire 284 extending from inner trace pad 266. Thus, outer, center and inner trace pads 262, 264 and 266, respectively, form independent electrical circuits with CPU 36.

Staple trace system 250 further includes a first resistive layer or coating 286 formed over anvil member 20. Second and third resistive layers 288 and 290 are provided between respective outer trace pads 256, 262 and center trace pads 258, 264 and between center trace pads 258, 264 and inner trace pads 260, 266 to maintain electrical isolation of all trace pads. Finally, an outer or fourth resistive layer 92 is applied over all of the prior discussed traces and coatings to electrically isolate them from the environment. While not specifically shown, multiple windows may be provided through the resistive coatings or layers to expose anvil member 20 to ends of the various traces and allow anvil member 20 to function as a common ground or return path for some or all of the electrical circuits with CPU 36.

Figure 22:
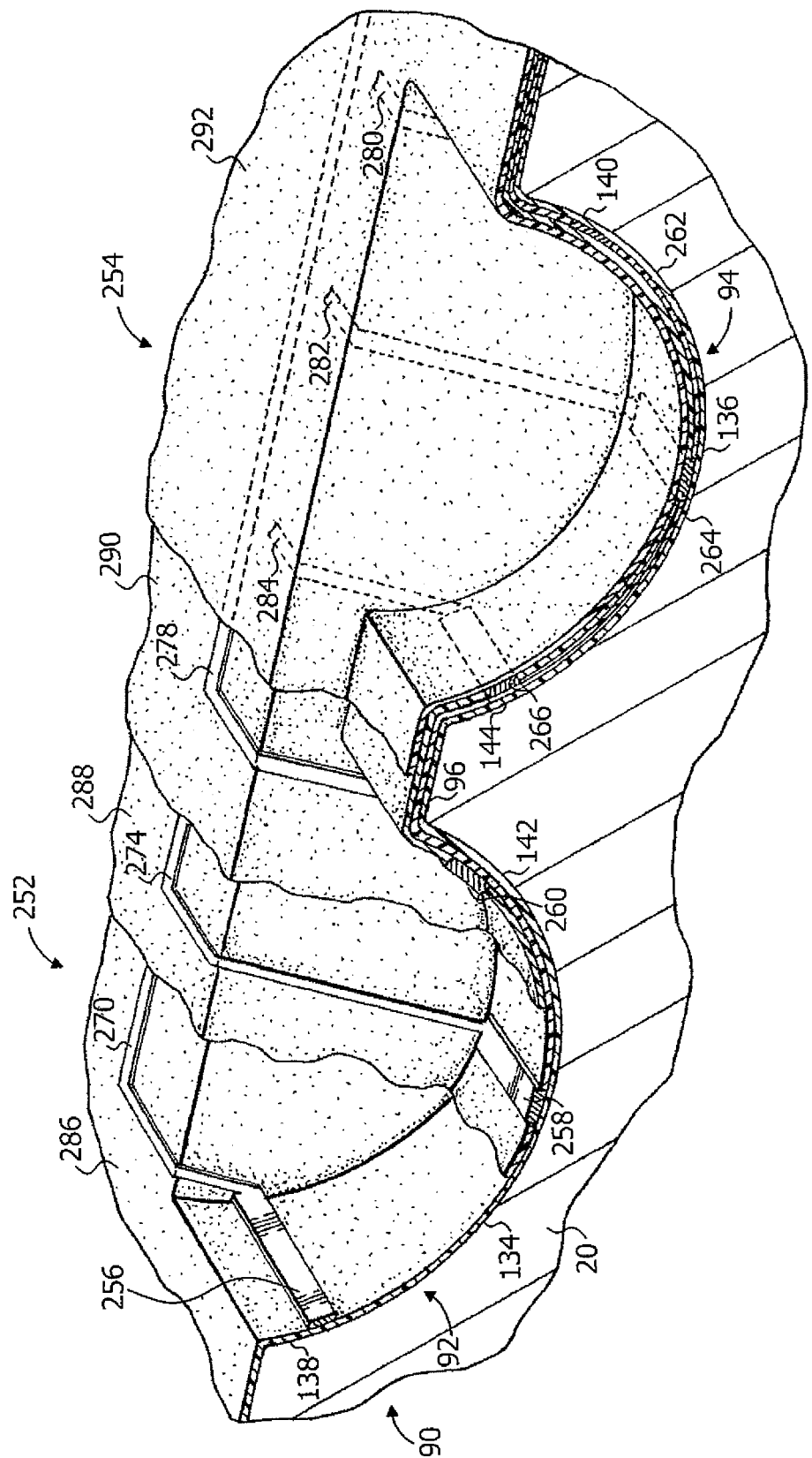
FIG. 22 is a cross-sectional view taken along lines 22-22 of FIG. 20.

Referring specifically now to FIG. 22, outer trace pads 256 and 262 are located along outer side edges 138 and 140 of staple pockets 92 and 94, respectively. Center trace pads 258 and 264 are located in bottoms 134 and 136 of staple pockets 92 and 94, respectively. Inner trace pads 260 and 266 are located along inner side edges 142 and 144, respectively, and adjacent central ridge 96 between staple pocket 92 and 94. As shown, first, second, third, fourth, fifth and sixth conductive wires 270, 274, 278, 280, 282 and 284, respectively, are layered between resistive coatings or layers 286, 288, 290, and 292 to electrically isolate them. This is accomplished in the manner described herein above with respect to wires 182, 198 and 200 and coatings 190, 192, 194 and 196 in FIG. 12a.

Figure 23:
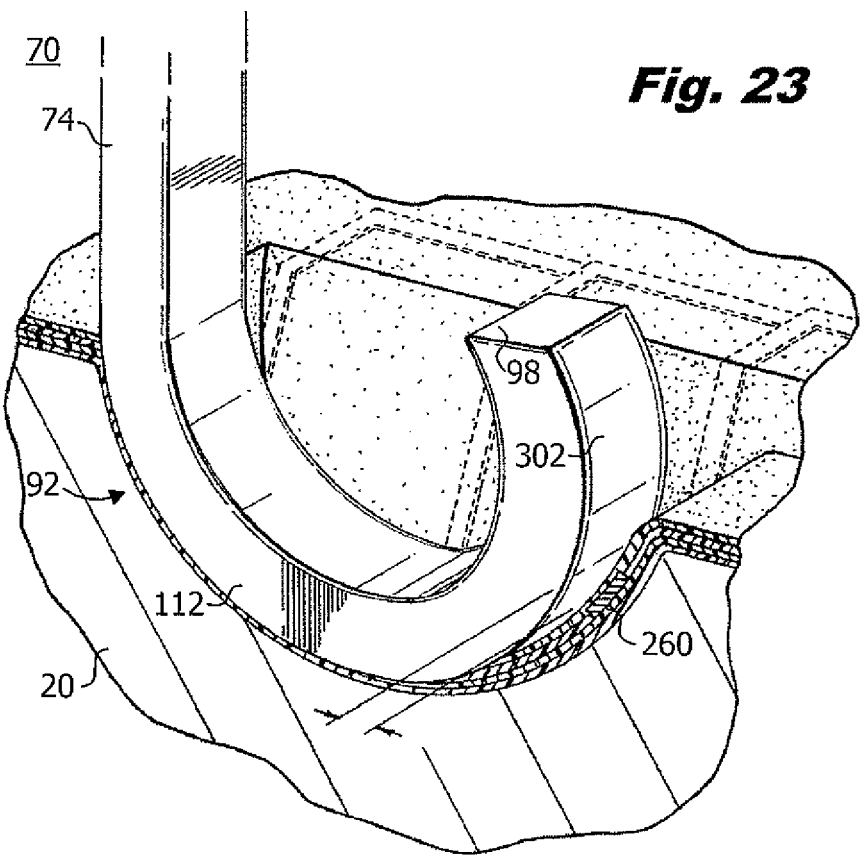
FIG. 23 is a cross-sectional view, partially shown in section, of a leg of a surgical staple contacting two of three trace pads of the staple trace system of FIG. 20.
Figure 24:
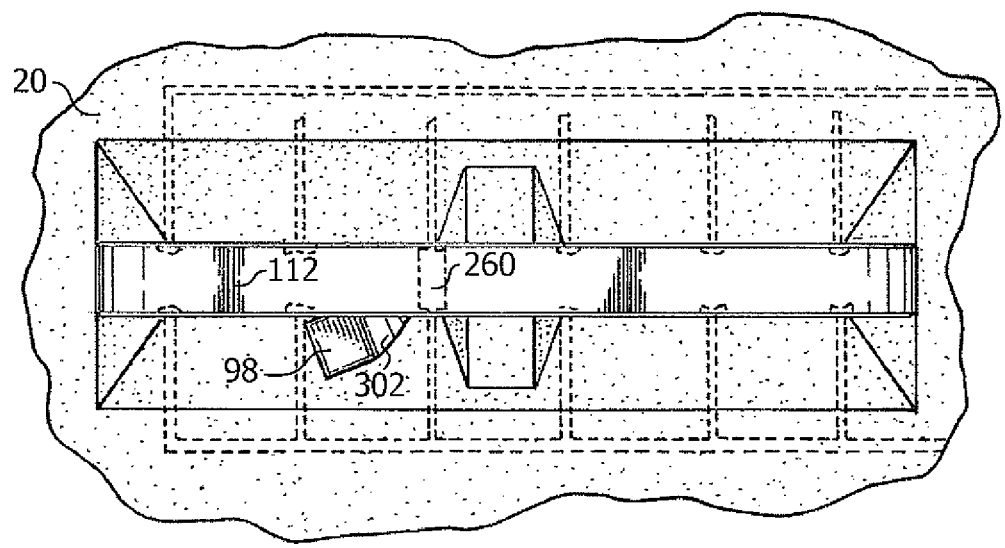
FIG. 24 is a top plan view of a surgical staple formed within a staple pocket of an anvil member and against the staple trace system of FIG. 20 and illustrating a tip of the staple leg angled away from the third trace pad of the staple trace system of FIG. 20.

Electrically resistive layers 288 and 290 may include windows or openings 294, 296 comment 298 and 300 to reduce the pressure required by surgical staple 70 passing through resistive layers 288 and 290 to contact trace pads 258, 264 and 260 and 266, respectively Referring now to FIGS. 22-24, in use, surgical staple 70 is formed in staple pockets 92 and 94 in the manner described herein above. When properly formed, outer trace pads 256, 262; center trace pads 258, 264 and inner trace pads 260, 266 of first and second trace arrays 252 and 254 is are broken through resistive layers 292, 290 and 288 to break or sever the electrical circuits with CPU 36 and display the proper staple formation on display screen 40. However, if a portion of a staple leg is not properly formed one of the traces will not be broken and that also will be indicated on display screen 40. For example, with regard to FIGS. 23 and 24, if tissue penetrating tip 98 of staple leg 74 is damaged or skewed along a length 302 of curved crimping portion 112, it may miss inner trace pad 260 and not break that electrical circuit with CPU 36. This will then be indicated on display screen 40 and the surgical procedure may be stopped and corrective action taken.

Thus, it can be seen that staple formation recognition or trace system 250, including separate first and second staple trace arrays 252 and 254, provide multiple independent locations for testing the proper formation of staple legs 74 and 76 of surgical staple 70 at various locations along the legs.

As noted hereinabove, surgical stapler 10 includes a knife position indicator system 50 on anvil member 20. Referring now to FIGS. 25-27, and initially with regard to FIG. 25, knife position indicator system 50 includes a knife position array system 310 to detect the position of knife blade 110 relative to a particular set of staple crimping pocket systems, such as, for example, staple crimping pocket systems 90, 90a, etc. and convey that information to the surgeon on display screen 40. This allows a surgeon to know if knife blade 110 has passed a location of improper staple formation and take precautionary and corrective actions.

Knife position array system 310 includes a plurality of trace pads 312-340 positioned in knife slot 44 and at respective locations S, S+1 through S+14 between staple crimping pocket systems 90, 90a, etc. For example, trace pad 312 is positioned within knife slot 44 at a location S between staple crimping pocket systems 90 and 90a. A final trace pad 342 is provided at a distal end 354 of knife slot 44 to confirm that knife blade 110 has fully passed through all the tissue captured between staple cartridge 22 and anvil member 20.

Referring to FIGS. 26 and 27, trace pad 312 is located across knife slot 44 to block passage of knife blade 110. Trace pads 312-342 are formed from conductive and frangible material that breaks sufficiently to prevent remnants from maintaining conductivity through knife blade 110 and across knife slot 44.

With specific reference to FIG. 27, trace pad 312 has conductive wires 346 and 348 which extend to CPU 36 through a cable 344 (FIG. 25). Conductive wire 346 and 348 are electrically isolated from anvil member 20 by a resistive coating or layer 350 and from the external environment by a resistive coating or layer 352.

Referring back to FIG. 25, as knife blade 110 passes through knife slot 44, it severs or breaks the trace pads positioned between staple crimping pocket systems 90, 90a, etc and follows the staple crimping actions occurring in those systems. CPU 36 receives the interruptions in the electrical circuits and transmits knife blade 110's location, i.e., S, S=1, etc., to display screen so the surgeon can monitor knife blade 110's progress along anvil member 20 relative to surgical staples 70 being properly or improperly formed as detected through one or more of the above described staple formation recognition system.

Furthermore, the sequence of staple formation and qualities of the individual formations may be recorded and compared to a predetermined sequence/array of qualities to determine the probability of staple line failure. The sequence of staple formation may be measured using a plurality of trace systems as described above. As the staples fire, the trace system signals the controller if a staple has entered its respective pair of staple crimping pockets 92, 94, and may record which pair of staple crimping pockets 92, 94 the signal is coming from. If the controller receives a signal from a sequentially first pair of staple crimping pocket 92, 94 (A1) that a first staple has fired, then a signal from a sequentially second pair of staple crimping pockets 92, 94 (A2) being immediately after A1 that a second staple has fired, the controller can determine that the first staple and second staple fired proper sequence. In an error situation, the controller may receive a signal from A1 that a first staple fired, then a signal from an arbitrary out of sequence pair of staple crimping pockets 92, 94 ($A_X$) that an out of sequence staple has fired. Since the controller would be expecting sequence A1-A2, but instead received A1-$A_X$, the controller can determine that an improper sequence has occurred and the there has been an error in staple firing. In the event that the first staple did not fire correctly, the first pair of staple crimping pockets 92, 94 outputting a signal would by necessity be $A_X$ allowing the computer to detect faulty sequence from the beginning of stapling.

As an example, A1 may be any individual or plurality of staple crimping pockets 92, 94 before S+4, and A2 may be any individual or plurality of staple crimping pockets 92, 94 between S+4 and S+7. In this case, $A_X$ may be an individual or plurality of staple crimping pockets 92, 94 that have staples sensed out of sequence such that if a staple is sensed in any individual or plurality of staple crimping pockets 92, 94 after S+7 before being sensed in A1 and A2, or if a staple is sensed in any individual or plurality of staple crimping pocket 92, 94 after S+4 before A1 is sensed, then the controller can determine that an error has occurred. This logic can be applied to work with any desired combination and desired sequence of staple crimping pockets 92, 94.

With respect to staple formation quality, a trace system in an individual anvil may allow the controller to determine first if a staple has fired by sensing if at least one of the trace pads in at least one of the anvil pockets 92, 94 senses at least one leg of the staple. Further, the controller can then compare a first anvil pocket 92 with a second anvil pocket 94 to determine if both pockets 92, 94 sense a leg to determine if both of the staple's legs have entered the anvil. Further formation quality may be determined by embodiments where multiple trace pads exist in each anvil pockets 92, 94 such that the controller can determine optimal B-type staple formation by sensing if each leg of staple has contacted the plurality of trace pads in each pocket, or at least which of the plurality of trace pads the staple legs have contacted.

In some embodiments, a controller may also read one or more properties of the trace system including resistance, inductance, impedance, or capacitance in one or more of a parallel or series circuit configuration. The controller may then compare these readings to other readings or a known database of values to determine the quality of stapling, sequence of stapling, etc.

Such sequence detection and quality analysis as described above may allow for detection of staple lines that will ultimately fail, open at the ends, etc., which would allow the clinician to recognize an improper staple location and change, modify, or reinforce the staple line to help prevent early staple line failure.

In some embodiments, the progression of the blade may be measured and compared against the sequence and quality of staple formation to ensure that stapling quality and cutting timing is occurring within a predetermined tolerance. The position of the blade may be measured using any means suitable including, but not limited to, encoders, microswitches, magnetic or displacement transducers, etc. If the detected sequence of staples and/or the relative position of the blade with respect to the stapling sequence fall outside a predetermined tolerance, a controller may stop further advancement of the blade, notify the clinician of an error state, signal the clinician to stop, or any combination thereof.

It will be understood that various modifications may be made to the embodiments disclosed herein. For example, the disclosed traces may extend longitudinally along the length of the staple pockets. Further, other means of signaling improper staple formation may be provided such as, for example, tactile, auditory, thermal, etc. Additionally, the traces need not be consecutively spaced but rather formed randomly along the length of the anvil member. Still further, the disclosed trace systems may be incorporated into the staple cartridge to confirm the full and complete ejection of the surgical staple out of the staple pockets. Therefore, the above description should not be construed as limiting, but merely as exemplifications of particular embodiments. Those skilled in the art will envision other modifications within the scope and spirit of the claims appended hereto.

The invention claimed is:

1. A staple formation recognition system for use with an anvil member of a surgical stapler, the staple formation recognition system comprising:
   an anvil member defining a staple crimping pocket system having first and second staple pockets;
   a trace system at least partially extending within the staple crimping pocket system; and a controller forming an open electrical circuit with the trace system, the open electrical circuit configured to close through a surgical staple when the surgical staple is properly formed.

2. The staple formation recognition system as recited in claim 1, wherein the trace system includes a first trace pad extending across the first staple pocket of the staple crimping pocket system.

3. The staple formation recognition system as recited in claim 2, wherein the trace system includes a second trace pad extending across the second staple pocket of the staple crimping pocket system, the open electrical circuit configured to close when a surgical staple contacts the first and second trace pads.

4. The staple formation recognition system as recited in claim 1, further comprising an electrically resistive layer positioned between the trace system and anvil member.

5. The staple formation recognition system as recited in claim 1, further comprising an electrically resistive layer applied over the trace system.

6. The staple formation recognition system as recited in claim 2, wherein the anvil member forms a second trace pad configured to engage a leg of a surgical staple to close the open electrical circuit.

7. The staple formation recognition system as recited in claim 6, further comprising an electrically resistive layer applied over the anvil member, the electrically resistive layer having a window configured to expose the anvil member to the leg of the surgical staple.

8. The staple formation recognition system of claim 1, wherein the controller is further configured to detect a sequence of staple formation and qualities of individual staple formations and compare the sequence of staple formation and qualities of the individual staple formations to a predetermined sequence/array of qualities to determine at least one probability of a staple line failure.

9. The staple formation recognition system of claim 1, wherein the controller reads one or more properties of the trace system including resistance, inductance, impedance, or capacitance.

10. The staple formation recognition system of claim 1, wherein the controller is configured to detect the relative position of a blade and compare the detected relative position with a sequence of staple formation to ensure that stapling and cutting is occurring within a predetermined tolerance.

11. The staple formation recognition system of claim 1, further comprising a plurality of trace systems disposed upon each other, each trace system of the plurality of trace systems being electrically insulated from another trace system of the plurality of trace systems by a resistive layer disposed between each trace system of the plurality of trace systems.

12. The staple formation recognition system of claim 2, wherein the first trace pad may be flat or shaped to follow a curvature of the first or second staple pocket.

13. A staple formation recognition system for use with an anvil member of a surgical stapler, the staple formation recognition system comprising:
 an anvil member defining a staple crimping pocket system having first and second staple pockets;
 a trace system at least partially extending within the staple crimping pocket system; and
 a controller forming an electrical circuit with the trace system, the electrical circuit configured to be interrupted by a surgical staple when the surgical staple is properly formed within the staple crimping pocket system.

14. The staple formation recognition system as recited in claim 13, wherein the trace system includes multiple trace pads extending across the first staple pocket.

15. The staple formation recognition system as recited in claim 13, wherein the trace system includes a first trace pad extending across the first staple pocket of the staple crimping pocket system.

16. The staple formation recognition system as recited in claim 15, wherein the trace system includes a second trace pad extending across the second staple pocket of the staple crimping pocket system, the electrical circuit configured to be interrupted when at least one of the first and second trace pads is broken by a leg of the surgical staple.

17. The staple formation recognition system as recited in claim 16, wherein the trace system includes first and second conductive wires extending from opposed ends of the first trace pad.

18. The staple formation recognition system as recited in claim 16, wherein the trace system is electrically isolated from the anvil member by an electrically resistive layer.

19. The staple formation recognition system as recited in claim 18, wherein the trace system includes a first conductive wire extending from a first end of the first trace pad and a second end of the first trace pad forms an electrically conductive path to the anvil member through an opening in the electrically resistive layer.

20. The staple formation recognition system as recited in claim 17, wherein one of the conductive wires forms a common electrical path with one end of a second trace pad in the second staple pocket.

* * * * *